(12) United States Patent
Sabry et al.

(10) Patent No.: US 6,743,576 B1
(45) Date of Patent: Jun. 1, 2004

(54) DATABASE SYSTEM FOR PREDICTIVE CELLULAR BIOINFORMATICS

(75) Inventors: James H. Sabry, San Francisco, CA (US); Cynthia L. Adams, Palo Alto, CA (US); Eugeni A. Vaisberg, Foster City, CA (US); Anne M. Crompton, San Francisco, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 09/311,890

(22) Filed: May 14, 1999

(51) Int. Cl.[7] .............. C12Q 1/00; C12M 1/00; G01N 1/00
(52) U.S. Cl. .............. 435/4; 422/50; 435/287.1
(58) Field of Search .............. 435/4, 287.1, 6, 435/7.1, 7.2, 183.1; 422/50, 68.1

(56) References Cited

U.S. PATENT DOCUMENTS

| | | | |
|---|---|---|---|
| 4,818,710 A | * 4/1989 | Sutherland et al. | 436/527 |
| 4,922,092 A | 5/1990 | Rushbrooke et al. | |
| 4,959,301 A | 9/1990 | Weaver et al. | 435/5 |
| 4,965,725 A | 10/1990 | Rutenberg | 364/413.1 |
| RE34,214 E | 4/1993 | Carlsson et al. | |
| 5,287,272 A | * 2/1994 | Rutenberg et al. | 364/413.01 |
| 5,326,691 A | 7/1994 | Hozier | 435/6 |
| 5,355,215 A | 10/1994 | Schroeder et al. | 356/317 |
| 5,526,258 A | 6/1996 | Bacus | |
| 5,548,661 A | 8/1996 | Price et al. | 382/133 |

(List continued on next page.)

FOREIGN PATENT DOCUMENTS

| | | |
|---|---|---|
| EP | 0468705 | 1/1992 |
| EP | 0317139 | 4/1998 |
| EP | 0902394 | 3/1999 |
| WO | WO 87/02802 | 5/1987 |
| WO | WO 93/21511 | 10/1993 |

(List continued on next page.)

OTHER PUBLICATIONS

Giuliano et al., "High-Content Screening: A New Approach to Easing Key Bottlenecks in the Drug Discovery Process", *J. Biomolecular Screening*, 2(4): 249–259 (1997).

Pauwels et al., "Determination of the Mechanism of Action of Anticancer Drugs by Means of the Computer-Assisted Microscope Image Analysis of Feulgen-Stained Nuclei", *J. Pharmacological and Toxicological Methods*, 37: 105–115 (1997).

(List continued on next page.)

*Primary Examiner*—Ardin H. Marschel
(74) *Attorney, Agent, or Firm*—Beyer Weaver & Thomas, LLP

(57) ABSTRACT

A system for acquiring knowledge from cellular information. The system has a database comprising a database management module ("DBMS"). The system also has a variety of modules, including a population module coupled to the DBMS for categorizing and storing a plurality of features (e.g., cell size, distance between cells, cell population, cell type) from an image acquisition device into the database. The system has a translation module coupled to the DBMS for defining a descriptor from a set of selected features from the plurality of features. In a specific embodiment, the descriptor is for a known or unknown compound, e.g., drug. A prediction module is coupled to the DBMS for selecting one of a plurality of a descriptors from known and unknown compounds from the database based upon a selected descriptor from a selected compound. The selected compound may be one that is useful for treatment of human beings or the like.

14 Claims, 29 Drawing Sheets

U.S. PATENT DOCUMENTS

| | | | |
|---|---|---|---|
| 5,655,028 A | 8/1997 | Soll et al. | 382/133 |
| 5,733,721 A | * 3/1998 | Hemstreet, III et al. | 435/6 |
| 5,741,648 A | 4/1998 | Hemstreet, III et al. | 435/6 |
| 5,776,748 A | 7/1998 | Singhvi et al. | 435/180 |
| 5,777,888 A | 7/1998 | Rine et al. | |
| 5,790,692 A | 8/1998 | Price et al. | 382/133 |
| 5,790,710 A | 8/1998 | Price et al. | 382/255 |
| 5,804,436 A | 9/1998 | Okun et al. | 435/286.1 |
| 5,856,665 A | 1/1999 | Price et al. | 250/205 |
| 5,893,095 A | 4/1999 | Jain et al. | |
| 5,919,646 A | 7/1999 | Okun et al. | 435/29 |
| 5,932,872 A | 8/1999 | Price | 250/201.3 |
| 5,962,520 A | 10/1999 | Smith et al. | |
| 5,976,825 A | 11/1999 | Hochman | 435/29 |
| 5,989,835 A | 11/1999 | Dunlay et al. | 435/7.2 |
| 5,991,028 A | 11/1999 | Cabib et al. | 356/346 |
| 5,995,143 A | 11/1999 | Price et al. | 348/345 |
| 6,007,996 A | 12/1999 | McNamara et al. | 435/6 |
| 6,008,010 A | 12/1999 | Greenberger et al. | 435/41 |
| 6,083,763 A | * 7/2000 | Balch | 436/518 |
| 6,103,479 A | 8/2000 | Taylor | |
| 6,146,830 A | 11/2000 | Friend et al. | |
| 6,222,093 B1 | 4/2001 | Marton et al. | |
| 6,345,115 B1 | 2/2002 | Ramm et al. | |

FOREIGN PATENT DOCUMENTS

| | | | |
|---|---|---|---|
| WO | WO 94/11841 | 5/1994 | G06F/15/70 |
| WO | WO 95/10036 | 4/1995 | |
| WO | WO 95/22749 | 8/1995 | |
| WO | WO 96/01438 | 1/1996 | |
| WO | WO 96/09605 | 3/1996 | |
| WO | WO 97/20198 | 6/1997 | |
| WO | WO 97/40055 | 10/1997 | |
| WO | WO 97/43732 | 11/1997 | |
| WO | WO 97/45730 | 12/1997 | |
| WO | WO 98/05959 | 2/1998 | |
| WO | WO 98/35256 | 8/1998 | |
| WO | WO 98/38490 | 9/1998 | |
| WO | WO 98/44333 | 10/1998 | |
| WO | WO 98/45704 | 10/1998 | |
| WO | WO 99/05323 | 2/1999 | |
| WO | WO 99/08091 | 2/1999 | |
| WO | WO 99/17116 | 4/1999 | |
| WO | WO 99/39184 | 8/1999 | |
| WO | WO 99/44062 | 9/1999 | |
| WO | WO 99/54494 | 10/1999 | |
| WO | WO 99/67739 | 12/1999 | |
| WO | WO 00/03246 | 1/2000 | |
| WO | WO 00/06774 | 2/2000 | |
| WO | WO 00/17624 | 3/2000 | |
| WO | WO 00/17643 | 3/2000 | |
| WO | WO 00/17808 | 3/2000 | |
| WO | WO 00/26408 | 5/2000 | |
| WO | WO 00/29984 | 5/2000 | |
| WO | WO 00/31534 | 6/2000 | |
| WO | WO 00/43820 | 7/2000 | |
| WO | WO 00/33250 | 8/2000 | |
| WO | WO 00/49540 | 8/2000 | |
| WO | WO 00/50872 | 8/2000 | |
| WO | WO 00/60356 | 10/2000 | |
| WO | WO 00/65472 | 11/2000 | G06F/17/00 |
| WO | WO 00/70528 A2 | 11/2000 | |

OTHER PUBLICATIONS

Pauwels et al., "Monitoring of chemotherapy–induced morphonuclear modifications by means of digital cell–image analysis", *J. Cancer Res. Clin. Oncol.*, 119:533–540 (1993).

Pauwels et al., "In Vitro Digital Cell Image Analysis of Morphonuclear Modifications Induced by Natural DNA–Interacting Anticancer Drugs in Three Neoplastic Cell Lines", *Meth. Find. Exp. Clin. Pharmacol.*, 17(3): 151–161 (1995).

Pauwels et al., "The Application of Computerized Analysis of Nuclear Images and Multivariate Analysis to the Understanding of the Effects of Antineoplastic Agents and Their Mechanism of Action", *Meth. Find. Exp. Clin. Pharmacol*, 15(2): 113–124 (1993).

Pauwels et al., "Combination of Computerized Morphonuclear and Multivariate Analyses to Characterize In Vitro the Antineoplastic Effect of Alkylating Agents", *J. Pharmacol. and Toxicol. Methods*, 33(1): 35–45 (1995).

Weinstein et al., "An Information–Intensive Approach to the Molecular Pharmacology of Cancer", *Science*, 275: 343–349 (Jan. 17, 1997).

Printout from Q3DM Website (www.Q3DM.com), printed on Mar. 1, 2001, 30 Pages.

Montironi R., et al., "Computer Cell Cycle and DNA Histogram Analyses in Image Cytometry in Breast Cancer", Journal of Clinical Pathology, GB, London, vol. 46, No. 9, Sep. 1993, pp. 795–800.

Giuliano K.A., et al., "Fluorescent–Protein Biosensors: New Tools for Drug Discovery", Trends in Biotechnology, GB, Elsevier Publications, Cambridge, vol. 16, No. 3, Mar. 1998, pp. 135–140.

Printout from Automated Cell Website (www.automatedcell.com) printed on Mar. 9, 2001, 24 Pages.

Blankenstein et al., "Modular concept of a laboratory on a chip for chemical and biochemical analysis," (1998) Biosensors & Bioelectronics 13:427–438.

Hartwell et al., "Integrating genetic approaches into the discovery of anticancer drugs," (1997) Science 278:1064–1068.

Hofland et al., "Role of tumor–derived fibroblasts in the growth of primary cultures of human breast–cancer cells: effects of epidermal growth factor and the somatostatin analogue octreotide," (1995) Int. J. Cancer: 60:93–99.

Ng et al., "Evaluating multi–dimensional indexing structures for images transformed by principal component analysis," Proceedings of SPIE, Bellingham, Spie, US (1996), vol. 2670, pp. 50–61.

Stearns et al., "Interleukin 10 (IL–10) inhibition of primary human prostate cell–induced angiogenesis: IL–10 stimulation of tissue inhibitor of metalloproteinase–1 and inhibition of matrix metalloproteinase (MMP)–2/MMP–9 secretion," (1999) Clin. Cancer Res. 5:189–196.

Takayama et al., "Patterning cells and their environments using multiple laminar fluid flows in capillary networks," (1999) Proc. Natl., Acad. Sci. USA 96:5545–5548.

Cseke, I., "A Fast Segmentation Scheme for White Blood Cell Images" (1992) IEEE, pp. 530–533.

Serbouti, S., et al., "Image Segmentation and Classification Methods for Detect Leukemias", (1991) Annual Int'l Conf. of IEEE Eng. In Medicine & Biology Soc., vol. 13, No. 1, pp. 0260–0261.

Adams, et al., "Cell Patterning on Glass and Polymeric Substrates", U.S. Provisional patent application No.: 60/138, 119, Filed Jun. 7, 1999, 17 Pages.

Rubas, et al., "An Integrated Method to Determine Epithelial Transport and Bioactivity of Oral Drug Candidates in Vitro" *Pharmaceutical Research*, vol. 13, No. 1, (1996) pp 23–27.

Sunblad et al., "The use of image analysis and automation for measuring mitotic index in apical confier meristems", © Oxford University Press 1998, Journal of Experimental Botany, vol. 49, No. 327, pp. 1749–1756.

Uria JA, Stahle–Backdahl M, Seiki M, Fueyo A, Lopez–Otin C, "Regulation of Collagenase–3 Expression on Human Breast Carcinomas in Mediated by Stromal–Epithelial Cell Interactions", Cancer Res Nov. 1, 1997; 57 (21):4882–8, Abstract.

* cited by examiner

Step 704 of Fig. 7A

Step 714 of Fig. 7B

Step 716 of Fig. 7B

Conversion of morphometric parameters into nucleic acid code and clustering of the resulting sequences using Neighbor Joining method.

| Compound: | Count | Area | Perimeter | Length | Breadth | Fiber length | Fiber breadth | Shape factor | Ell. form factor | Inner radius | Outer radius | Mean radius | Equiv. radius | Equiv. sphere vol. | Equiv. prolate vol. | Equiv. oblate vol. | Equiv. sphere surface area | Average gray value | Total gray value | Optical density | Radial dispersion | Texture Difference Moment | EFA Harmonic 2, Semi-Major | EFA Harmonic 2, Semi-Minor |
|---|---|---|---|---|---|---|---|---|---|---|---|---|---|---|---|---|---|---|---|---|---|---|---|---|
| Control | t | t | t | t | t | t | t | t | t | t | t | t | t | t | t | t | t | t | t | t | t | a | t | t |
| Taxol | a | t | t | t | t | t | t | a | t | t | t | t | t | t | t | t | t | t | t | t | t | t | t | t |
| CD | c | a | a | a | t | a | t | t | c | a | a | a | a | a | a | a | a | t | a | a | a | t | a | g |
| Nocodozol | c | t | t | t | t | t | t | t | t | t | t | t | t | t | t | t | t | t | t | t | t | t | t | t |
| Staurosporine | g | g | c | a | a | t | a | a | t | g | a | a | a | t | g | g | g | a | a | t | a | t | a | a |
| Vinblastine | c | t | t | t | t | t | t | t | t | t | t | t | t | t | t | t | t | t | t | g | t | t | t | t |
| Hydroxyurea | g | t | t | t | t | t | t | g | t | t | t | t | t | t | t | t | t | t | t | t | c | t | a | t |

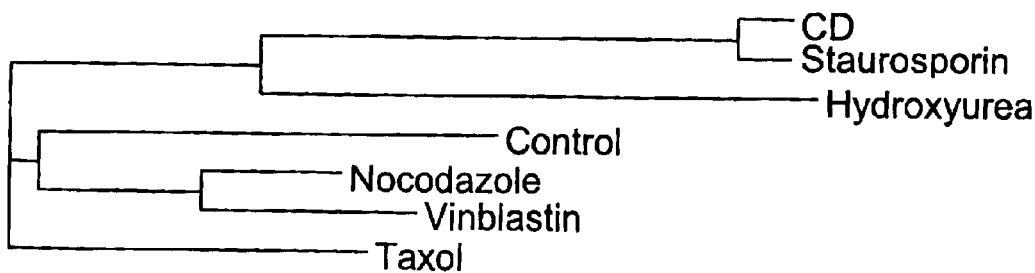

FIG. 18

DATABASE SYSTEM FOR PREDICTIVE CELLULAR BIOINFORMATICS

CROSS-REFERENCES TO RELATED APPLICATIONS

The following commonly-owned co-pending applications, including this one, are being filed concurrently and the others are hereby incorporated by reference in their entirety for all purposes:

1. U.S. patent application Ser. No. 09/310,879, James H. Sabry, et. al., titled, "A DATABASE METHOD FOR PREDICTIVE CELLULAR BIOINFORMATICS,";

2. U.S. patent application Ser. No. 09/311,890, James H. Sabry, et. al., titled, "A DATABASE SYSTEM FOR PREDICTIVE CELLULAR BIOINFORMATICS,";

3. U.S. patent application Ser. No. 60/134,104, Cynthia L. Adams, et. al., titled, "A DATABASE SYSTEM AND USER INTERFACE FOR PREDICTIVE CELLULAR BIOINFORMATICS,"; and 4. U.S. patent application Ser. No. 09/311,996, Eugeni A. Vaisberg, et. al., titled, "A DATABASE SYSTEM INCLUDING COMPUTER CODE FOR PREDICTIVE CELLULAR BIONFORMATICS,".

COPYRIGHT NOTICE

The present description includes examples of computer codes, which may be used to implement aspects of the present invention. Assignee of the present invention reserves all rights with respect to these codes and provides notice herein. Notice is hereby given © Cytokinetics, Inc. 1999.

BACKGROUND OF THE INVENTION

The present invention provides techniques for information management using a database platform. More particularly, the present invention provides a system including computer code that couples to a database device. The system provides for image capturing of living, dead, or fixed cells or cell fractions used to identify information about substances used on the cells or information about the cells themselves. Accordingly, the present invention can enable researchers and scientists to identify promising candidates in the search for new and better medicines, for example, in drug discovery and development. Other applications can also exist.

For a long time, researchers in the pharmaceutical field have sought for better ways of searching for substances possessing properties that make them suitable as medicines. In the early days, researches generally relied upon extracts from plants, dyes, and microbiological extracts for such substances. Examples of such substances include the pain reliever aspirin, the anti-cancer drug paclitaxel (brand name Taxol™), and the heart medication called digoxin. The number of useful medicines has generally been limited.

Purified substances having desirable bio-active properties are also often difficult to discover. Advances in traditional organic chemistry and more recently the rapid chemical synthesis methods often referred to as combinatorial chemistry have increased the number of compounds that researchers test for biological activity. Originally, substances were often initially tested on animals or humans to determine their biological activity. While results from such tests may identify a good drug candidate, they are often time consuming and costly, thus a limited number of substances can be tested. Therefore, pharmaceutical companies have turned to testing their ever-increasing libraries of substances against isolated proteins (drug targets) in biochemical assays that can be carried out at high throughput and low cost. It should be noted that the substances need to be tested in numerous protein tests, each customized for a particular drug target. Therefore, although each protein test may be run at a high-throughput, the design of multiple protein tests can be time-consuming. Substances deemed promising based on results from the protein tests are then tested in lower throughput cellular and animal tests.

There have been some attempts to use image acquisition techniques to screen a large number of molecular compounds based upon biological cell information. One such attempt is described in International Application No. WO 98/38490 in the names of Dunlay, et al. Dunlay et al. generally describes a conventional image acquisition system. This conventional system collects and saves images based on certain criteria that are predefined, not on a fixed area of an imaging surface. Additionally, the conventional system has poor lighting design, which makes image processing for multiple cells difficult. Furthermore, the conventional system is not designed for capturing, populating and utilizing a large database design. The conventional system is designed for customized cellular assays, not as a tool for generation of a cellular informatics database. Without such database capabilities the conventional system cannot be used for screening, analyzing, and comparing large quantities of cells from multiple experiments on multiple days in a predictive, efficient and cost effective manner.

What is needed is a rapid assay to assess the activity of compounds against multiple drug targets simultaneously in a cellular context. What is also needed are techniques for finding the effects of substances on cell function based upon searching and analyzing cellular information.

SUMMARY OF THE INVENTION

According to the present invention, techniques for determining information about effects of potential therapeutic compounds on cells is provided. In an exemplary embodiment, the present invention provides a novel system including hardware, computer codes, and a database for storing and retrieving cellular and substance information. The cells can include living, dead, or fixed cells or fractions of cells.

In a specific embodiment, the present invention provides a system for acquiring knowledge from cellular information. The system has a database comprising a database management module ("DBMS"). The system also has a variety of modules, including a population module coupled to the DBMS for categorizing and storing a plurality of features (including population cellular features such as cell size, distance between cells, cell population, as well as sub-cellular features such as organelle location, protein location and sub-cellular constituent location and movement) from an image acquisition device into the database. The system has a translation module coupled to the DBMS for defining a descriptor from a set of selected features from the plurality of features. In a specific embodiment, the descriptor is for a known or unknown compound, e.g., drug. A prediction module is coupled to the DBMS for selecting one of a plurality of a descriptors from known and unknown compounds from the database based upon a selected descriptor from a selected compound. The selected compound may be one that is useful for treatment of human beings or the like.

In a specific embodiment, the present invention provides a system for populating a database with cellular information. The system includes a cell holder (e.g., multi-well plate, chip, microfluidic assembly, or other cell chamber) comprising a plurality of sites in a spatial orientation. Each of the sites is capable of holding a plurality of cells to be imaged. Preferably, the present system also has an illumination apparatus comprising a liquid light guide operably coupled to the imaging device for highlighting the plurality of cells in a relatively even spatial manner for image capturing and measurement purposes. Still further, the liquid light guide allows sub-elements (e.g., filter, lamp) of the illumination apparatus to be placed at a remote location to prevent mechanical interference of the cell holder during image capturing. The system also has an image-capturing device (e.g., charge coupled device camera, translation stage, shutter, microscope, software, shutter control) coupled to a computing device (e.g., computer, network computer, work station, analog computing device, on-board image-processor, and laptop). The image-capturing device is adapted to capture at least one image in at least one of the plurality of sites. One some embodiments, multiple images can be captured, where each image represents a different cell component (or portion). The image-capturing device can be adapted to convert the image into a digital representation, which highlights the feature or features of the one site. A database storage device (e.g., relational database, object oriented database, mixed object oriented database) includes a database management clement. The database is coupled to the image capturing device. In a specific embodiment, the present system includes modules for feature extraction, generation of descriptions, and data preparation and analysis.

In a specific embodiment, the present invention provides a novel system for determining an effect of a manipulation of a cell using one or more image frames. The system has a plate comprising a plurality of sites in a spatial orientation. Each of the sites is capable of holding a plurality of cells to be imaged. The system also has an image capturing device to capture a plurality of images of at least one site from the plurality of sites. The image capturing device is coupled to the computing device. The system also has an image processing device to combine the plurality of images of at least one site or plurality of sites. The image processing device is operably coupled to the plate. An image processing device is also included. The image processing device can be adapted to form a digitized representation of the plurality of images from the site or plurality of sites. Furthermore, the system has a database storage device comprising a database management element. The database can be adapted to retrieve the descriptor or descriptors of the plurality of features from the computing processing device and storing them in a selected manner.

In a specific embodiment, the present invention provides a system for capturing cellular information. The system also has an image acquisition system comprising a charged coupled device camera adapted to capture an image of a plurality of manipulated cells in various stages of the cell cycle. The stages of the cell cycle include interphase, prophase, metaphase, anaphase, and telophase. An optical source is coupled to the image acquisition system for highlighting the plurality of manipulated cells in the various stages of the cell cycle. The illumination apparatus provides for an acquisition of the image of the plurality of manipulated cells. In a specific embodiment, the illumination apparatus has a liquid light guide coupled to a light source at a remote location.

Numerous benefits are achieved by way of the present invention over conventional techniques. The present invention can provide techniques for predictive cellular bioinformatics that can streamline a number of important decisions made in the drug discovery industry. The present invention can be implemented using off the shelf hardware including databases. In other aspects, the present invention can find useful information about substances as well as cells or portions of cells. Furthermore, the present invention can acquire more then one feature using more than one manipulation. Moreover, the present invention can provide information about a wide variety of cellular information that is not conventionally available. This information includes information about different cell constituents, e.g., nuclei and golgi apparatus. Still further, the present invention provides an automated or semi-automated technique for acquiring images and populating a database. The present database can be combined with others such as genomics, and the like. Moreover, the present invention can be implemented to predicting a mechanism of action, toxicity, target validation, pre-clinical disease model selection, pharmacokinetic properties, pharmacodynamic properties, metabolism, excretion, absorption, distribution, and the like. The present invention also can be used for diagnostic and prognostics including predicting what drug combination works, what is the prognosis, when cells used come from a specific patient. Depending upon the embodiment, one or more of these advantages may be present. These and other benefits are described throughout the present specification.

A further understanding of the nature and advantages of the invention herein may be realized by reference to the remaining sections of the specification and the attached drawings.

BRIEF DESCRIPTION OF THE DRAWINGS

FIG. 8A–8F illustrate representative quantified descriptors of effects of manipulations on images of cells in a particular experiment wherein FIG. 8A shows the histogram for average intensity; FIG. 8B shows histogram data for the area of each object; FIG. 8C shows the scatter plot of the average intensity vs. the area of all of the objects; FIG. 8D shows a graph where each type of cellular classification is delimited; FIG. 8E shows a bar graph of the average and standard deviations of the areas for each cell classification type; FIG. 8F shows a bar graph of the average and standard deviations of the average intensities for each cell classification type;

FIG. 18 shows the results of conversion of morphometric parameters into nucleic acid code and clustering of the resulting sequences using Neighbor Joining methods;

DESCRIPTION OF THE SPECIFIC EMBODIMENTS

According to the present invention, techniques for determining information about manipulated cells or substances based upon living, fixed, or dead cells or portions of cells are provided. In an exemplary embodiment, the present invention provides a novel system including computer codes coupled to a database for storing and retrieving such information. Other embodiments provide a novel image capturing system for providing digitized representations of live and dead cell structures or the like. An embodiment according to the present invention is marketed under the name Cytometrix™, which may not intended to be limiting. All rights are reserved with respect to this mark.

Figure 1:
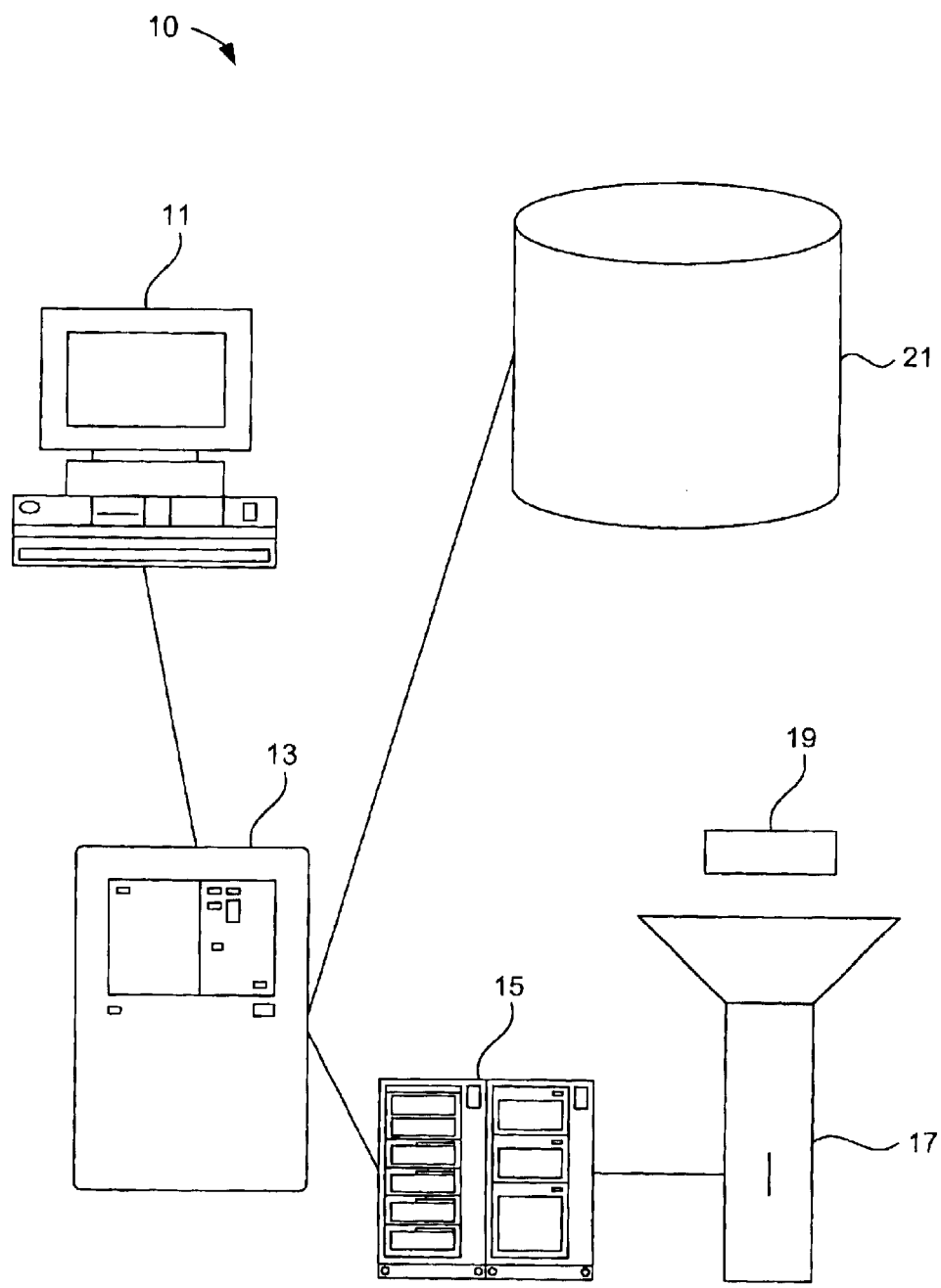
FIG. 1 is a simplified system diagram of a cellular knowledge-based system according to an embodiment according to the present invention.

FIG. 1 is a simplified system diagram 10 of a cellular knowledge-based system according to an embodiment according to the present invention. This diagram is merely an example and should not limit the scope of the claims herein. One of ordinary skill in the art would recognize other variations, modifications, and alternatives. The present system 10 includes a variety of elements such as a computing device 13, which is coupled to an image processor 15 and is coupled to a database 21. The image processor receives information from an image capturing device 17, which are collectively referred to as the imaging system herein. The image capturing device obtains information from a plate 19, which includes a plurality of sites for cells. These cells can be biological cells that are living, fixed, dead, cell fractions, cells in a tissue, and the like. The computing device retrieves the information, which has been digitized, from the image processing device and stores such information into the database. A user interface device 11, which can be a personal computer, a work station, a network computer, a personal digital assistant, or the like, is coupled to the computing device.

Figure 1A:
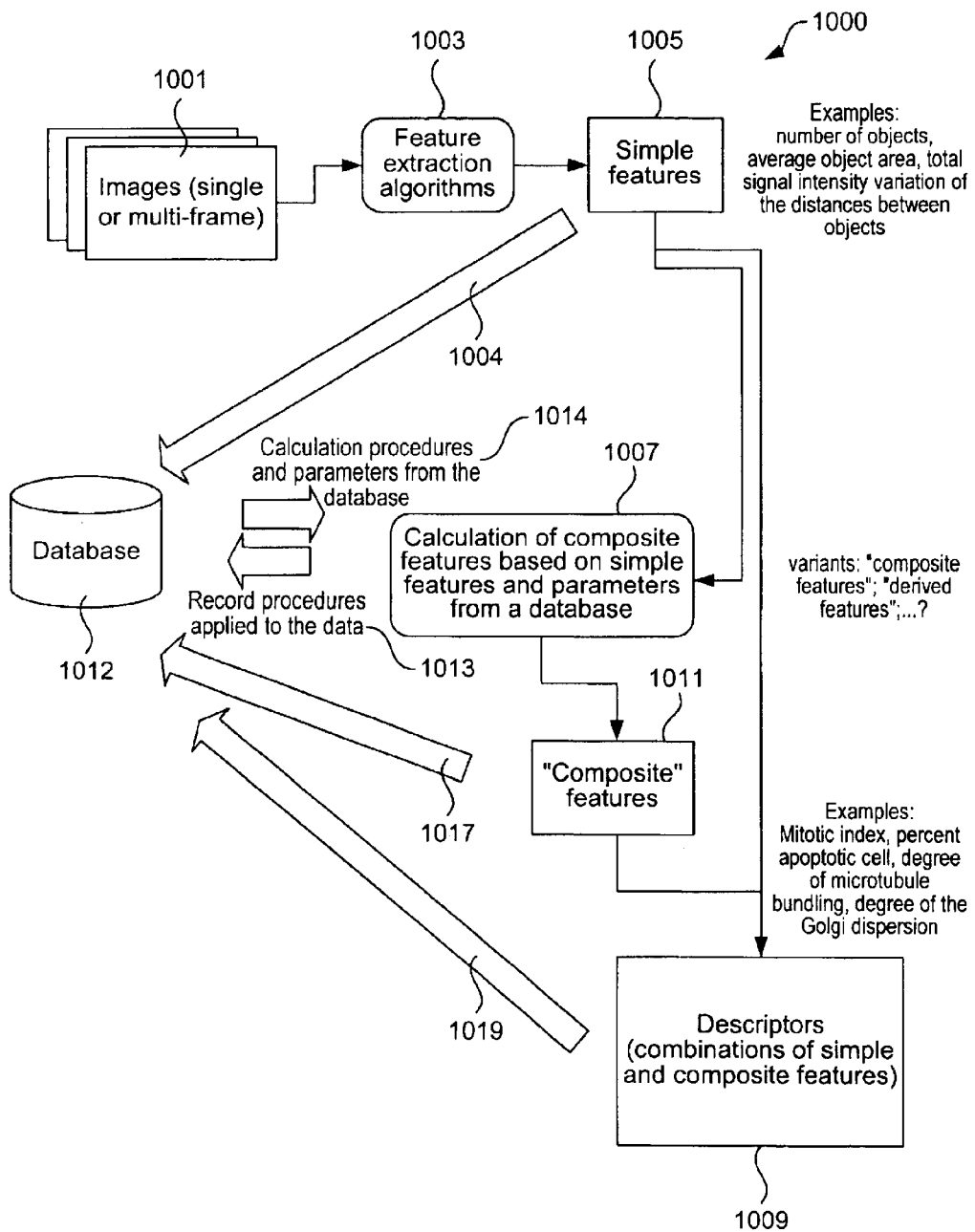
FIG. 1A is a simplified diagram of a database system 1000 according to an embodiment of the present invention.

FIG. 1A is a simplified diagram of a database system 1000 according to an embodiment of the present invention. This diagram is merely an example and should not limit the scope of the claims herein. One of ordinary skill in the art would recognize many other variations, modifications, and alternatives. Database system 1000 includes a variety of techniques for processing images from biological cells, e.g., fixed, living, and dead cells, and cell portions. As shown, images are acquired 1001. These images can be from a single frame or multiple frames. As merely an example, an image processing system may analyze such images. An example of such an image processing system is described below, but should not be construed as limiting certain claims. A further example of processing techniques is described in more detail in U.S. Ser. No. 09/311,890 noted above. Each image is of a cell portion or a plurality of portions, which are digitized representation(s).

In a specific embodiment, cell samples are manipulated using a compound (e.g., substance, drug). The cell samples are imaged for a simple portion or portions, e.g., manipuated cell substructure, manipulated spatial feature of cell, cell density. Image processing techniques are used to extract 1003 the feature or features from the image or images. The features can be an independent or a dependent set of cell characteristics (which may be predominately visual) including, for example, count, area, perimeter, length, breadth, fiber length, fiber breadth, shape factor, elliptical form factor, inner radius, outer radius, mean radius, equivalent radius, equivalent sphere volume, equivalent prolate volume, equivalent oblate volume, equivalent sphere surface, average intensity, total intensity, optical density, radial dispersion, texture difference, and others. Each of these features correspond to a similar manipulation by a compound. Each manipulation forms a new set of features, which are identifiable to the compound. Once each set of features has been extracted, the feature set is populated 1004 into a database 1012. Accordingly, the database includes many sets of features, where each set corresponds to a different manipulation for a selected cell. Each set of features corresponding to a manipulation provides a descriptor 1009, which is also stored 1019 in the database. The descriptor is a "finger print" including each feature for the manipulation. Ideally, each descriptor is unique, but will have similarities or may even be the same as other descriptors for known and unknown manipulations.

The present system retrieves features, which we define as simple features herein, and forms composite features 1007 from them. More than one feature can be combined in a variety of different ways to form these composite features. In particular, the composite feature can be any function or combination of a simple feature and other composite features. The function can be algebraic, logical, sinusoidal, logarithmic, linear, hyperbolic, and the like. Alternatively, more than one simple feature can be combined in a functional manner (e.g., arithmetic, algebraic). As merely an example, the composite feature equals a sum of feature 1 and feature 2, where these features correspond to the same manipulation. Alternatively, the composite feature equals feature 1 divided by feature 2. Alternatively, the composite feature equals feature 1 minus feature 2. Alternatively, the composite feature equals a constant times feature 1 plus feature 2. Of course, there are many ways that the composite feature can be defined. The present system also stores 1017 these features in the database. The composite features can also be further combined with simple features. Once these features are defined as descriptors, they are stored 1019 in the database.

Figure 1B:
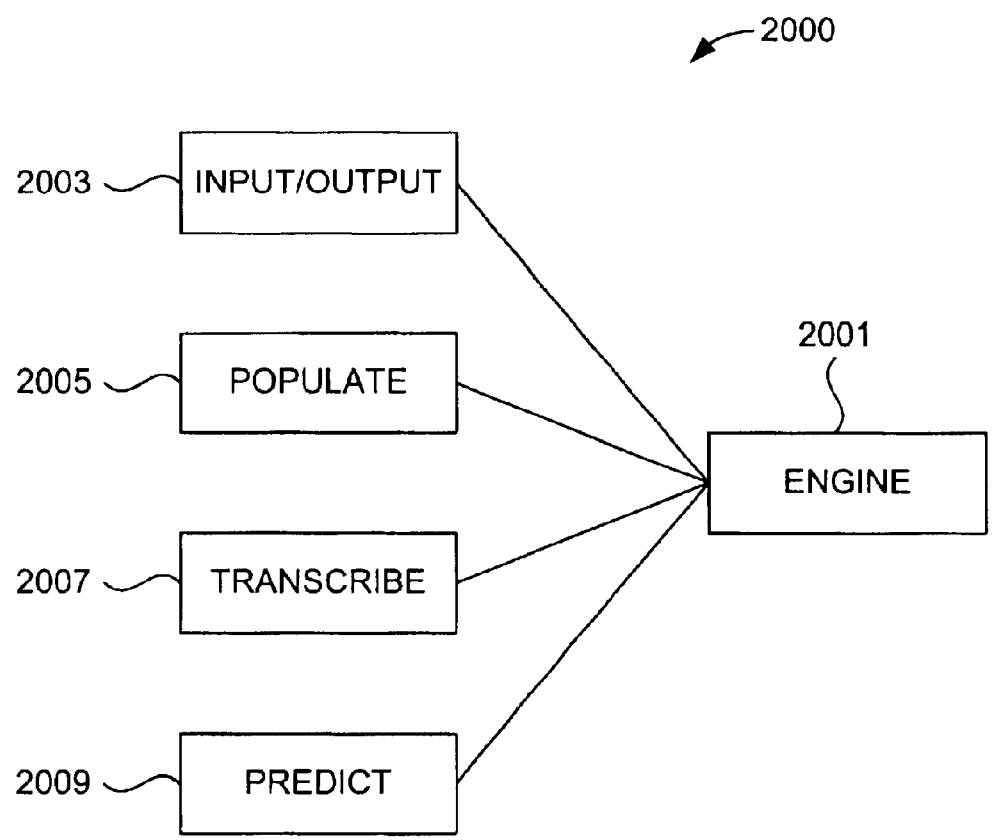
FIG. 1B is a simplified diagram of a database system engine 2000 according to an embodiment of the present invention.

FIG. 1B is a simplified diagram of a database system engine 2000 according to an embodiment of the present invention. This diagram is merely an example and should not limit the scope of the claims herein. One of ordinary skill in the art would recognize many other variations, modifications, and alternatives. The engine can be implemented into the present database for populating, searching, and predicting compound or cell characteristics. As merely an example, engine 2001 includes an input/output module 2008. The input/output module is used to input and output information from the database. The information includes, among others, a plurality of feature sets, which correspond to many manipulations. Additionally, the information includes descriptors, which each corresponds to a set of features from the manipulation. The database also has a population module, which is used to configure the features based upon an entity relationship, which has been predetermined.

The database engine also has other modules. In particular, the database has a transcription module, which transfers a preselected set of features and creates a descriptor from them. The transcription module can be used to take a known compound, which has features, to transcribe them into a descriptor. Alternatively, the transcription module can be used to take an unknown compound, which has features, to transcribe them into a descriptor. These descriptors are provided into the database for subsequent use. Finally, the database engine has a prediction module, which can be used to potentially predict a property (e.g., mechanism of action) of an unknown compound. Here, the unknown compound is provided with a descriptor, but the property of the compound is unknown. In one embodiment, the prediction module compares a descriptor of an unknown compound with the many descriptors of known compounds, which were in the populated database. Depending upon the matching criteria, the prediction module will attempt to uncover one or more descriptors of known compounds. Once the prediction module finds the descriptors of the known compounds based upon the descriptor for the unknown compound, it identifies a potential property of such unknown compound for analysis and review. Here, it is believed that certain features of the known compound, which are similar to those features of the unknown compound may uncover a property to the unknown compound. Details of the present software engine are described more fully below.

Figure 2:
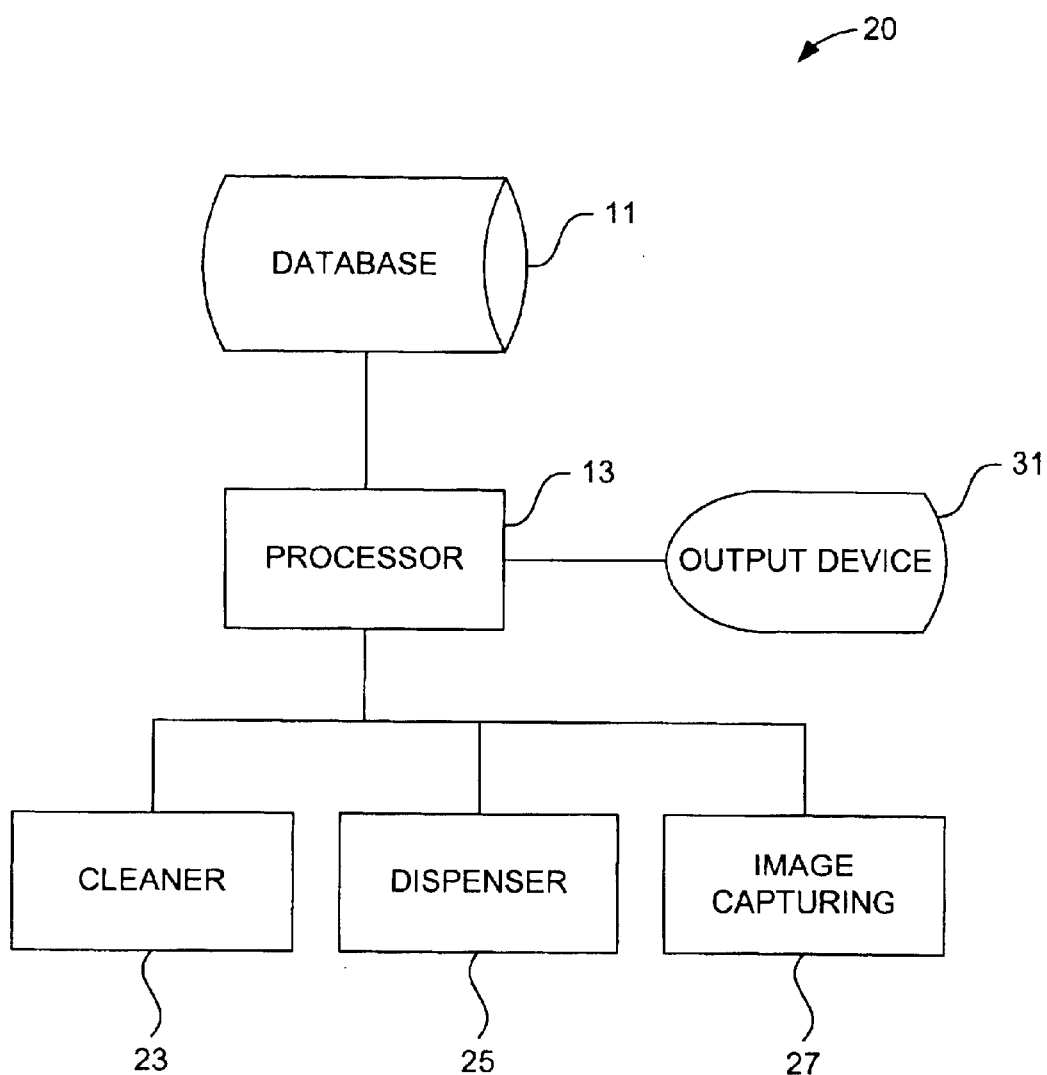
FIG. 2 is a simplified block diagram according to an alternative embodiment according to the present invention.

FIG. 2 is a simplified block diagram 20 of a cellular knowledge-based system according to an alternative embodiment of the present invention. This diagram is merely an example and should not limit the scope of the claims herein. One of ordinary skill in the art would recognize other variations, modifications, and alternatives. Like reference numerals are used in the present diagram as the previous diagram for easy cross-referencing, but are not intended to be limiting in any manner. The present diagram 20 includes a variety of elements such as a processor 13 or computing device coupled to a database 11. The processor can be used for retrieving and storing information from the database. The system also includes a plurality of system elements, such as a cleaner 23, a dispenser 25, and an image capturing system 27, which are also coupled to the database in some embodiments. These elements can be coupled to each other through a network or the like. As merely an example, the network can be a NetWare™ network from Novell Corporation or an internet network or the Internet but can also be others and any combination thereof. The system also has an output device 31, which can be used to output information from the database, processor, or other system elements. Details of these elements are described more fully below in reference to the Figs.

Figure 3:
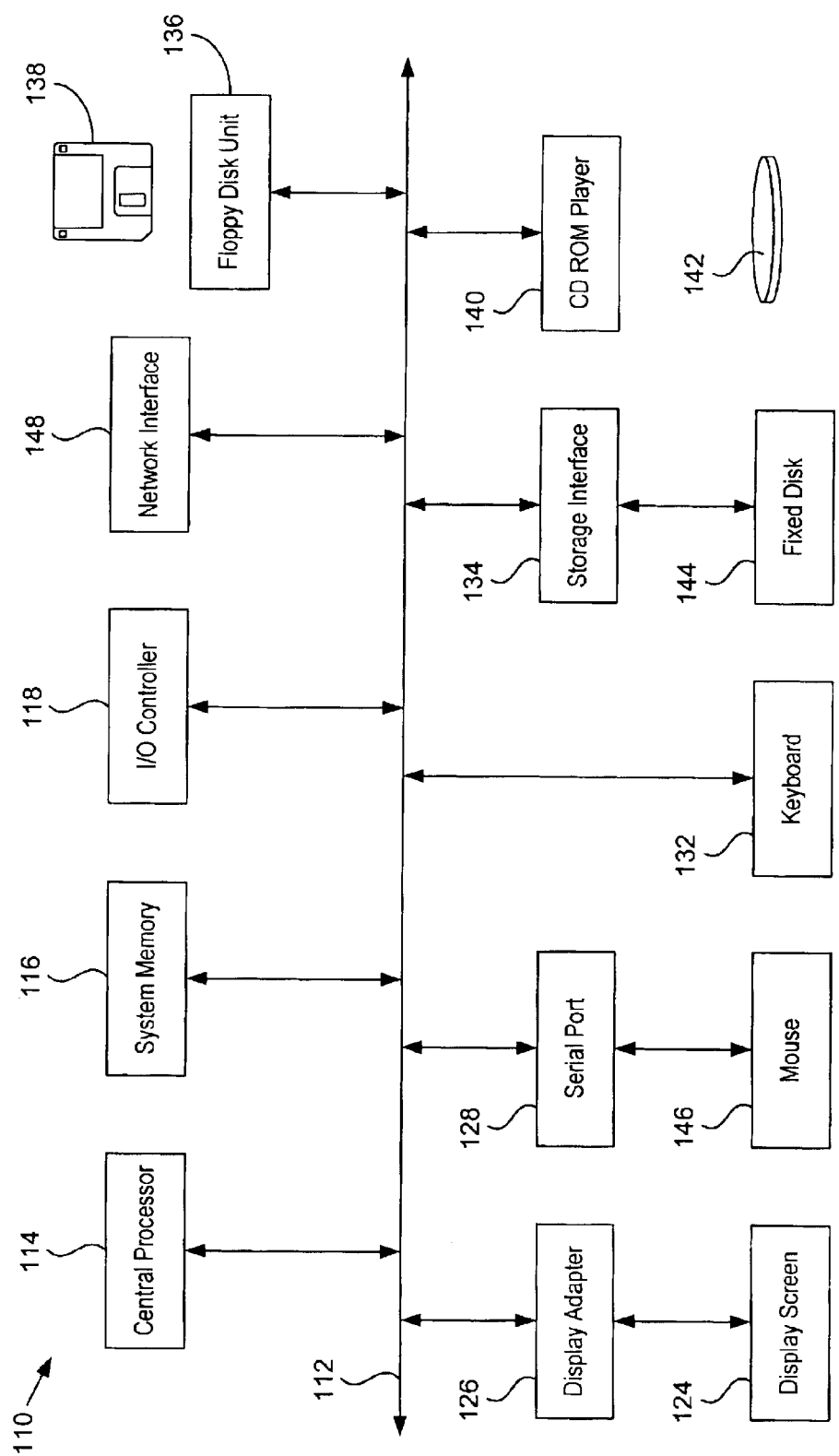
FIG. 3 is a simplified diagram of a processor or computing device 13.
Figure 4:
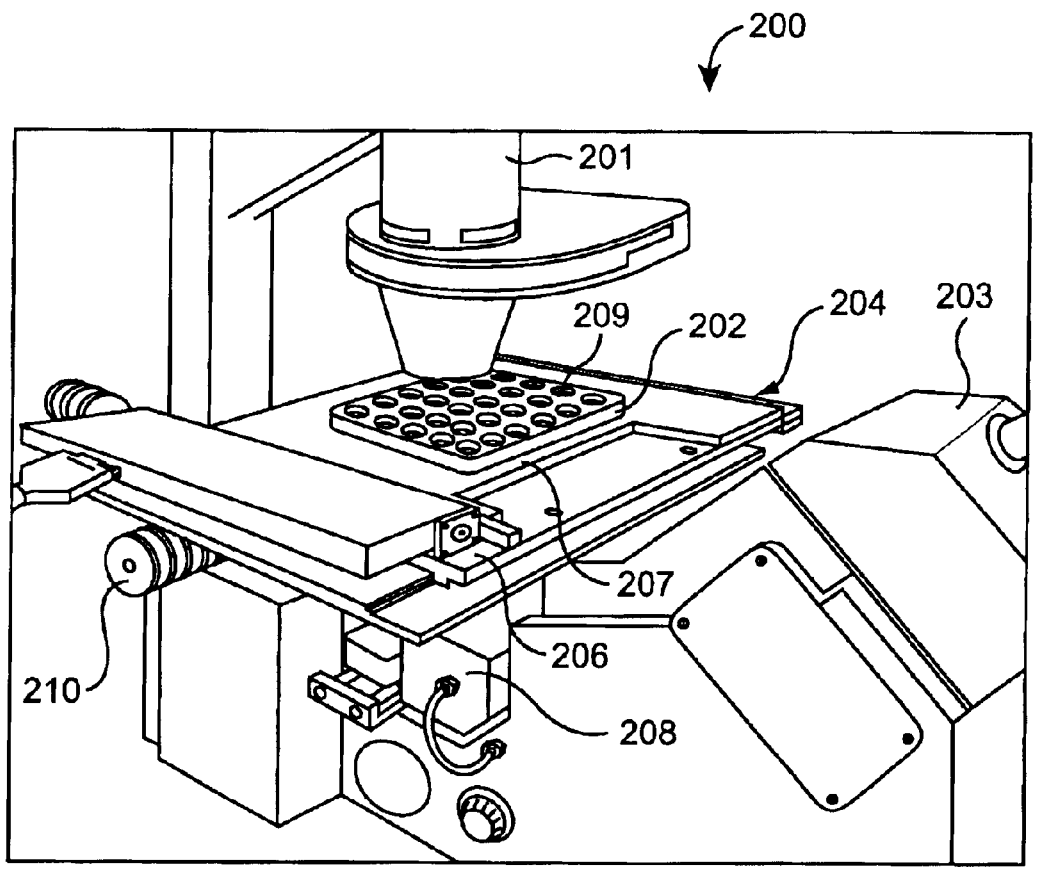
FIG. 4 is a simplified diagram of an imaging system 200 according to an embodiment of the present invention.
Figure 5:
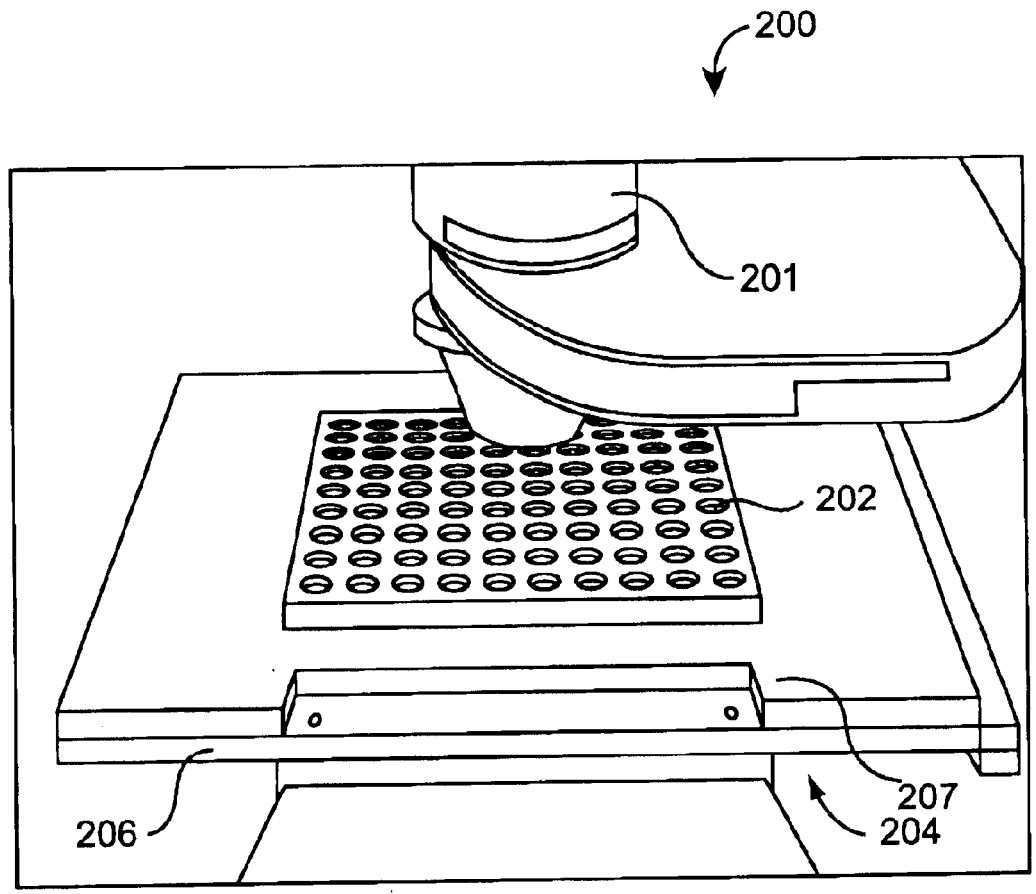
FIG. 5 is a more detailed diagram of an imaging system 200 according to an embodiment of the present invention with the present embodiment of the imaging system being shown in FIGS. 5A and 5B.

FIGS. 3–5 are simplified drawings of system elements according to embodiments of the present invention. These diagrams are merely examples and should not limit the scope of the claims herein. One of ordinary skill in the art would recognize other variations, modifications, and alternatives. As merely an example, FIG. 3 is a simplified diagram of a processor or computing device 13. The computing device 13 includes a bus 112 which interconnects major subsystems such as a central processor 114, a system memory 116 (e.g., random access memory), an input/output ("I/O") controller 118, an external device such as a display screen 124 via a display adapter 126, a keyboard 132 and a mouse 146 via an I/O controller 118, a SCSI host adapter (not shown), and a floppy disk drive 136 operative to receive a floppy disk 138.

The computing device has other features. Storage Interface 134 may act as a storage interface to a fixed disk drive 144 or a CD-ROM player 140 operative to receive a CD-ROM 142. Fixed disk 144 may be a part of computing device or may be separate and accessed through other interface systems. A network interface 148 may provide a direct connection to a remote server via a telephone link or to the Internet. Network interface 148 may also connect to a local area network ("LAN") or other network interconnecting many computer systems. Many other devices or subsystems (not shown) may be connected in a similar manner. Also, it is not necessary for all of the devices shown in FIG. 3 to be present to practice the present invention, as discussed below. The devices and subsystems may be interconnected in different ways from that shown in FIG. 3. The operation of a computer system such as that shown in FIG. 3 is readily known in the art and is not discussed in detail in this application. Computer code to implement the present invention, may be operably disposed or stored in computer-readable storage media such as system memory 116, fixed disk 144, CD-ROM 140, or floppy disk 138. The computer code can be organized in terms of processes or modules, depending upon the application. That is, the computer code can include a prediction module, a translation, module, or other modules to carryout the functionality described herein, as well as others.

FIGS. 4 and 5 are simplified diagrams of an imaging system 200 according to an embodiment of the present invention. As shown, the imaging system 200 includes a variety of features such as housing 203, which holds a stage assembly 204. The stage assembly includes an x-stage movement element 206, which is along an x-direction, and a y-stage movement element 207, which is along a y-direction. The imaging system also includes a z-direction movement element, which is perpendicular to the x-y plane. The z-direction movement motor can be attached to the stage, or to the objective nosepiece by way of the microscope housing, or as an external motor between the objective and the microscope housing. The stage can align in any one of the directions to an accuracy of one micron and less, or one-half micron and less, or one-quarter micron and less, depending upon the embodiment.

The stage holds a plate 202 or cell holder, which houses one of a plurality of samples. The plate includes a spatial array 209 of process sites. Each of the process sites can include a plurality of cells and solutions depending upon the embodiment. Each of the sites can carry a sufficient amount of solution to prevent substantial evaporation of the sample during processing in some embodiments. In embodiments for large scale analysis, the plate includes at least 96 sites, or more than or equal to 384 sites, or more than or equal to 1,536 sites. The plate bottom is transparent and thin, which allows light to pass through the sample. Additionally, the plate is made of a suitable chemical resistant material. As merely an example, the plate can be either a 96, or 384, or 1536 or other formats from places such as Becton Dickinson of Franklin Lakes, N.J., or Corning Science Products of Corning, N.Y. In a preferred embodiment, the plate is a Coming Costar black-walled 96 well plate catalog #3904 from Corning Science Products of Corning, N.Y., but should not be limited to these in some applications, but can be others.

Also shown is the condenser for the microscope 201, which can be used to collect phase, DIC, or bright field images of the cells. Images resulting from the illumination of the samples to fluorescence, phase, DIC, or bright field techniques are collected using an image capturing device 208, which captures an image or images of cells from the plate. In a specific embodiment, the microscope is an inverted configuration with the objectives on the bottom of the plate and the condenser disposed overlying an upper surface of the sites, while the image capturing device underlies the sites. Images captured by the imaging device, whether analogue or digital, are viewed by a monitor or other devices. The image capturing device can be any camera assembly such as a charge coupled device camera, which is known as a CCD camera, or other high resolution camera capable of capturing images from the sites. In a specific embodiment, the camera is an interline CCD camera which does not require an external shutter.

In a specific embodiment, the present imaging system can be any suitable unit that is flexible for automated image collection using multi-well plastic plates. The imaging system also should be adapted to collect high-resolution images of cells on plastic or glass plates, cell growth chambers, or coverslips. The system also can be used for imaging multiple cell markers in multiple imaging conditions. To accomplish this, the microscope system has a variety of elements such as a light source, a motorized excitation filter wheel and shutter, x-y-z-motorized stage, excitation and emission filters, Fluor phase and DIC objectives, motorized objective nosepiece, dichroic filters, motorized dichroic filter cubes, phase and DIC rings and prisms, CCD camera, and software control. As merely an example, the present imaging system can have components such as those listed in the Table below.

TABLE

Image Acquisition System Elements

| DESCRIPTION | MAKER | MODEL |
| --- | --- | --- |
| Microscope | Zeiss | 100 M |
| (x-y) motorized stage | Prior | |
| Xenon lamp | Sutter | Lambda |
| Filter wheel | Sutter | Lambda-10 |
| Microtitre Plate holder | Prior | 500-H223R |
| Isolation Table | Kinetic Systems | 9101-24-85 |
| Objective Spacers | Polytec PI | P-721.90 |
| Camera | Hamamatsu | C47-95 |
| Computer | IBM | IntelliStation |
| Software | Metamorph | v.4 |
| Objectives | Zeiss | Achroplan 10x/0.25 |
| | | LD-Achroplan 20x/0.4 |
| | | LD-Achroplan 40x/0.6 |

In a specific embodiment, the present system has the following capabilities, which are not intended to be limiting.

Image acquisition
1) Ability to automatically acquire multi-wavelength images from multiple sites on one multi-well plate, to sequentially name image files, and to log any imaging parameter information with image files.
2) Ability to link images with a larger database/spreadsheet of information.
3) Ability to automatically collect multiple plates by interfacing the imaging system with a robotic arm.

X-Y control
1) Ability to place 96, 384, or 1536 well plates onto microscope stage and move to each well sequentially.
2) Ability to return to each well and collect another round of images (multi-site time-lapse) or ability to collect rapid time-lapse information at each well (time-lapse of many wells).
3) Ability to collect a low magnification image, automatically determine features which may be of interest, automatically change the objective to a higher magnification, and collect high magnification images of a fixed number of those identified cells in the sample.
4) Ability to collect multiple frames in each site.

Z control
1. Ability to auto-focus with substantially minimal damage to biological specimen or fluorophore.
2. Ability to auto-focus rapidly.

Figure 5A:
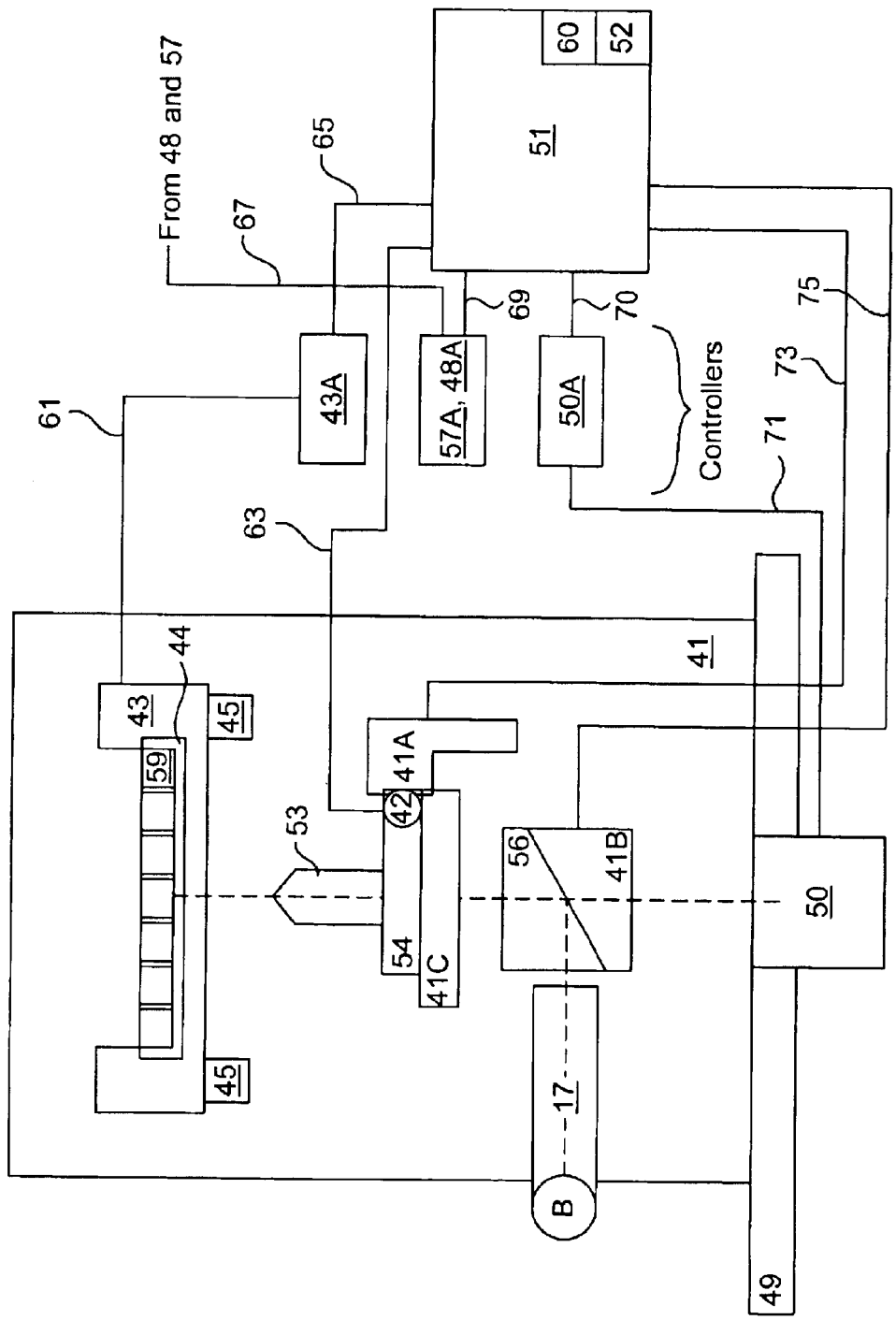
Figure 5B:
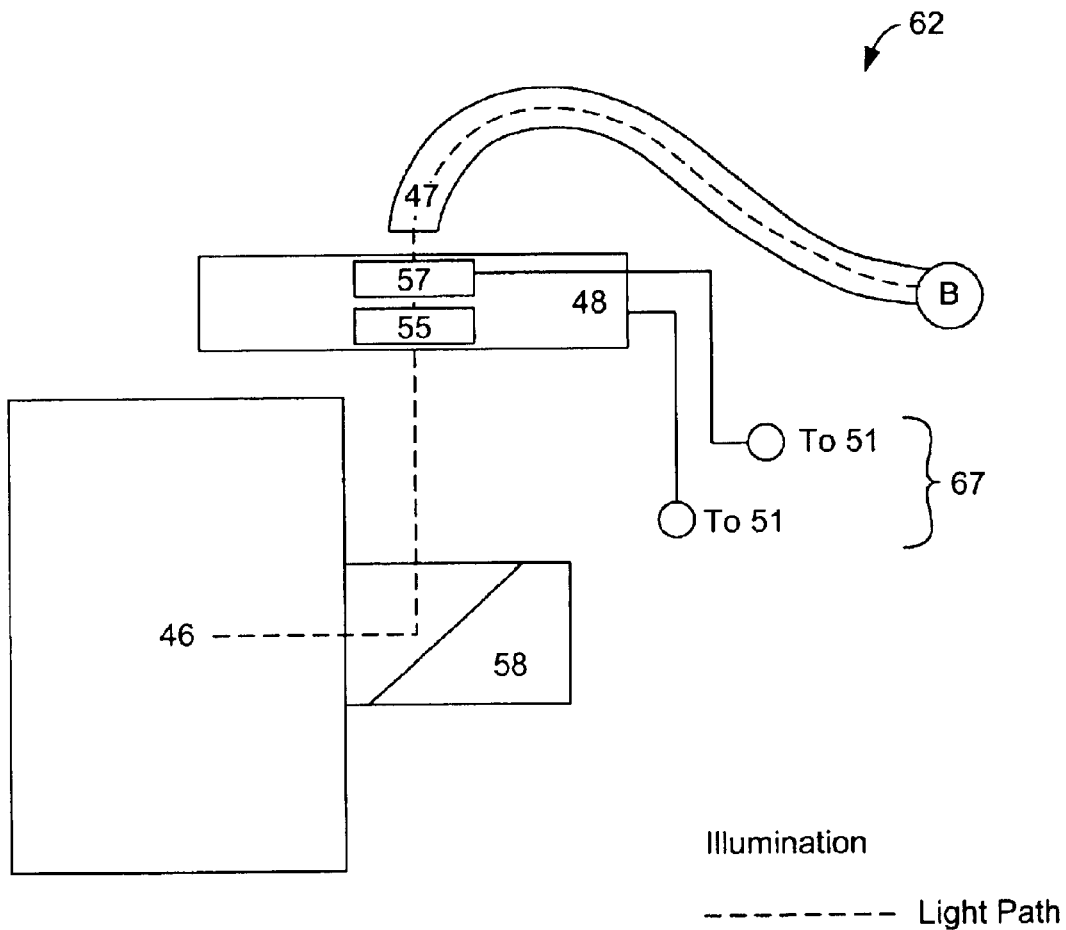

The present embodiment of the imaging system is shown by way of FIGS. 5A and 5B. These diagrams are merely examples and should not limit the scope of the claims herein. One of ordinary skill in the art would recognize other variations, modifications, and alternatives. The present imaging system 40 includes a variety of elements such as a microscope 41, which is preferably an epi-fluorescent microscope, but can be confocal, multiphoton, or hybrid types. The microscope includes elements 41A, the motorized Z-axis; 41B, the motorized dichroic filter cube holder; and 41C, the motorized objective nosepiece. In one embodiment, the microscope is a Model 100M made by Zeiss. The microscope communicates to computer 51 through control lines 73, 75, and 76. The imaging system also has camera 50 coupled to controller 50A and computing device 51, which oversees and controls operations of the elements of the imaging system.

The present microscope includes drivers for spatially moving a stage in two dimensions, including an x-direction, a y-direction, and moving the objective nosepiece in a z-direction in a Cartesian coordinate system. The z-direction movement is provided using a fast z-motor, which can make z-direction adjustments within a predetermined time. The z-direction movement generally provides for focussing of the sample to the camera. The focussing occurs within the predetermined time of preferably ten seconds and less, or five seconds and less, or one second and less, depending upon the embodiment. As merely an example, the z-motor or positioner can be a model PIFOC objective nanopositioner made by a company called Physik Instrumente of Waldbronn, Germany, but also can be others. The z-motor couples to computer 51 through line 63, which may also include a controller. Depending upon the embodiment, a second z-motor 41A connected to the computer 51 by line 73 may be used to keep the z-motor 42 in the center of its travel. Alternatively, in other embodiments the stage could be provided with a z-motor allowing for movement of the stage in the z-direction.

The present stage also includes an x-y stage 43. The x-y stage moves plate 59, e.g., 96 site, 384 site, 1536 site. The x-y stage moves plate in an x-y spatial manner. The stage has an accuracy or repeatability of about 1 micron and less, or about 2 microns and less. The stage can move in a continuous manner or a stepped manner. The stage also can move up to 30 mm/sec. or faster. The stage also can move 1 mm/sec. and less, depending upon the embodiment. The stage can also step 0.1 micron and less or 1 micron and less, as well as other spatial dimensions. The stage can be one such as a Proscan Series made by Prior Scientific of Rockland, Mass. but can also be others. The stage is controlled via control line 61 through controller 43A, which couples to computer 51 through control line 65.

The stage includes plate holder 44. The plate holder can hold a single plate. In other embodiments, plate holder can also hold multiple plates. The plate holder can use mechanical, electrical, fluid, vacuum and other means for holding the plate or plates. The plate holder also is sufficiently stable for securing the plate. As merely an example, the plate holder is a Model 500-H223R made by Prior Scientific of Rockland, Mass. In some embodiments, the plate holder may need adjustment in the z-direction to provide for a desirable focus of a sample on a plate. In these embodiments, the plate holder is supported by spacers 45 or a plurality of stage pins, which mechanically elevate the plate holder in the z-direction. These pins are generally made of a suitable material for supporting such plate holder and also are sufficiently resistant to chemicals and the like.

In some embodiments, the entire imaging system is placed on an isolation table 49. The isolation table is disposed between the microscope and support structure. The isolation table is designed to prevent excessive vibration of the plate. The isolation table is made of a suitable material such as steel and honeycomb but can be others. The table has a thickness of about 8 inches or preferably less than about 24 inches. In one embodiment, the table is Model 9101-24-85 made by Kinetic Systems of Boston, Mass.

The imaging system also has a lamp or illumination assembly 62. The lamp assembly provides for a light source (See reference letter B) to a plurality of elements in the imaging system. For easy reading, the light path is defined by the doted lines, which are not intended to be limiting. The lamp assembly has a variety of elements such as a Xenon lamp 46. The Xenon lamp provides light at about 320 to 700 nanometers (Prefocused). The Xenon lamp is 175 or 300 Watts. As merely an example, the lamp can be a Lambda Model made by Sutter Instrument Company of Novato, Calif.

Referring to FIG. 5B, the lamp assembly also has a cold mirror 58, an excitation filter wheel 48, excitation filter(s) 55, and an excitation light shutter 57. As shown, light is derived from the Xenon lamp, reflects off of the cold mirror 58, traverses through the excitation filter or filters 55, and is controlled by the excitation light shutter 57. The lamp assembly has filter wheel 48, which houses one of a plurality of filters, including excitation filters. The shutter and filter wheel are controlled via control lines 67, which are coupled to a computer 51 or other type of computing device. The control lines 67 are coupled through controller 57A (for element 57) and controller 48A (for element 48) via control line 69 to computer 51.

Preferably, light traverses from the lamp assembly through a light guide 47 to illuminate features within the plate. The light guide is suitably selected to have a flexible member, which can be used to place lamp source at a remote location away from the imaging device. The flexible member substantially keeps any vibration from the lamp assembly away from the imaging device. In some embodiments, the member is at least 1 foot away from the imaging device. The light guide is a guide, which is a flexible hose-type sleeve. The sleeve is filled with a liquid such as an aqueous solution containing chloride or phosphate. A thin layer may be formed on the inside of the sleeve. The layer can be a containing tetrafluoroethylene and mexafluoropropylene, or containing tetrafluoroethylene and perfluoromethyl vinyl ether, or tetrafluoroethylene and perfluoropropyl vinyl ether. An example of such a light guide is described in International Application No. WO/98/38537 filed Feb. 29, 1997, and assigned to NATH, Gunther. The liquid light guide has less than about 30% transmission loss of the light at a remote location such as the imaging system.

Light is derived from the lamp assembly and directs off of filter 56, which directs the light upward. Filter 56 can be a dichroic and emission filter, as well as others. The light traverses through microscope nosepiece 41C, and traverses through objective spacers 54. An objective 53 magnifies the light toward a predetermined point on the plate 59. The objective can be, for example, made by Zeiss of Jena, Germany, as well as other companies. The objective can be one of a plurality including 1X, 10X, 20X, 40X, and others, depending upon the application. Magnification can be further expanded or contracted by intermediate optics between the objective and the camera. Selection of filter or filters is controlled by computer 51 via control line 75.

The camera 50 captures an image of cells from plate 59. The image is obtained from light scattering off of cells or portions of cells in the plate through objective 53, through objective spacers, through filters 56, which are captured at camera 50. In this preferred embodiment, the camera is a digital camera, but can be an analogue camera. The digital camera is a CCD camera, which has 1280 by 1024 pixels, or more or less. The pixels can be 6.7 microns in dimension or more or less. The camera preferably is substantially free from an external shutter to quickly capture a plurality of images of cells from the plate. The camera is controlled via control line 71 through controller 50A, which connects to computer 51 through control line 70. The present invention can also include other types of image acquisition devices selected from at least an epifluorescence, a confocal, a total-internal reflection, a phase, a Hoffman, a bright field, a dark field, a differential interference contrast, an interference reflection, or multi-photon illumination device.

The present imaging system stores images on a high density memory device 60. The high density memory device is preferably optical, but can also be magnetic. The high density memory device can be any suitable unit that is capable of storing a plurality of images from a plurality of sites in the plate. The memory device can be a compact disk, which would generally use a compact disk burner or the like. Depending upon the embodiment, the high density memory device is used to archive the images that are captured from the camera in the imaging system. Further details of the imaging system can be found throughout the present specification, and more particularly below.

Figure 6:
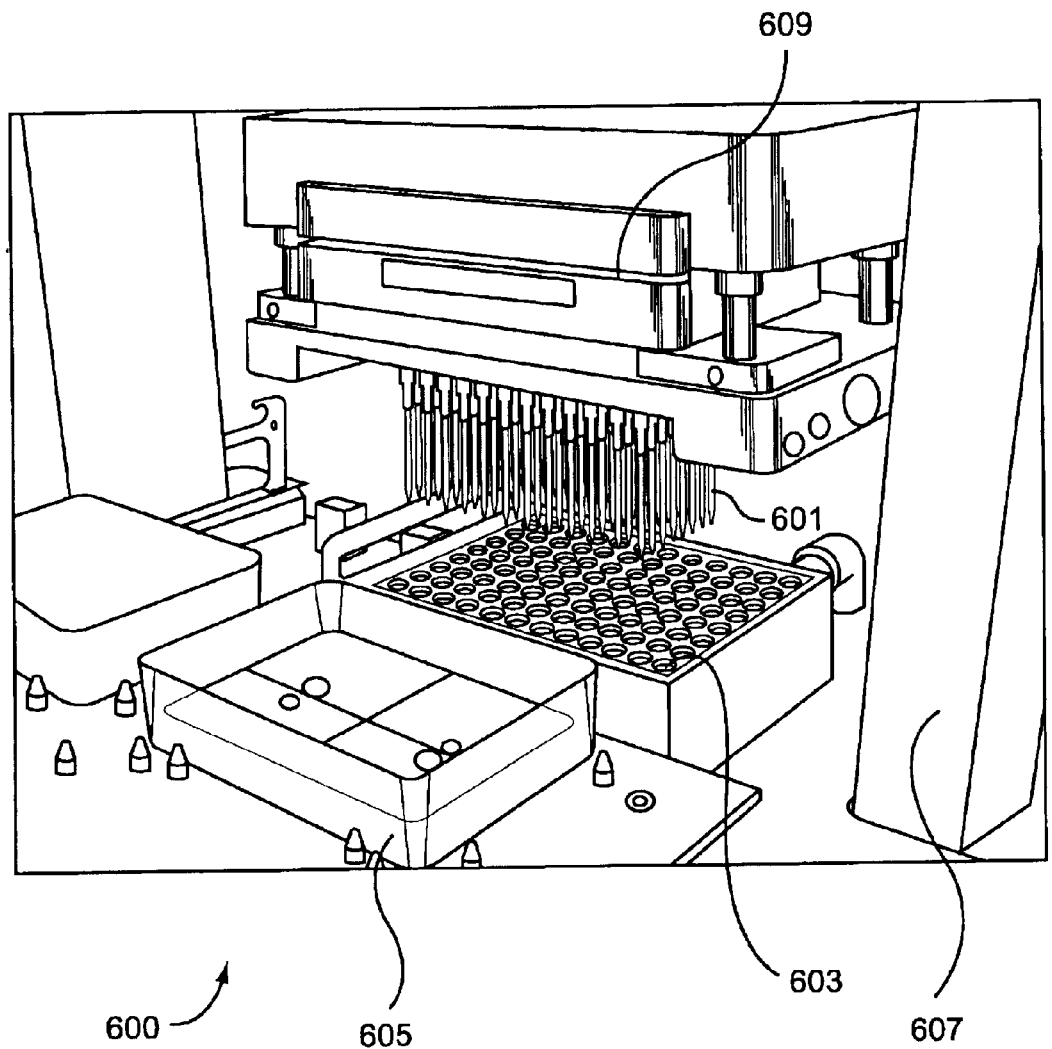
FIG. 6 is a simplified diagram 600 of a cleaning and dispensing system according to an embodiment of the present invention.

FIG. 6 is a simplified diagram 600 of a cleaning and dispensing system according to an embodiment of the present invention. This system 600 includes a variety of elements such as a dispensing head 609, which is coupled to a plurality of pipettes 601. The pipettes input and output fluids or solutions from plate 603. The plate has a plurality of sites, each of which can be used to input cells or a combination of cells and solution. The system also has elements to house solutions 605, which are used to manipulate cell samples in the plate. The dispensing head is supported through a support member 607, which is sufficiently rigid to allow for movement of the head. The dispenser is coupled to the present system in a mechanical and electrical manner, which provides for a fully integrated system for providing cell samples to the imaging system according to the present invention.

Figure 7A:
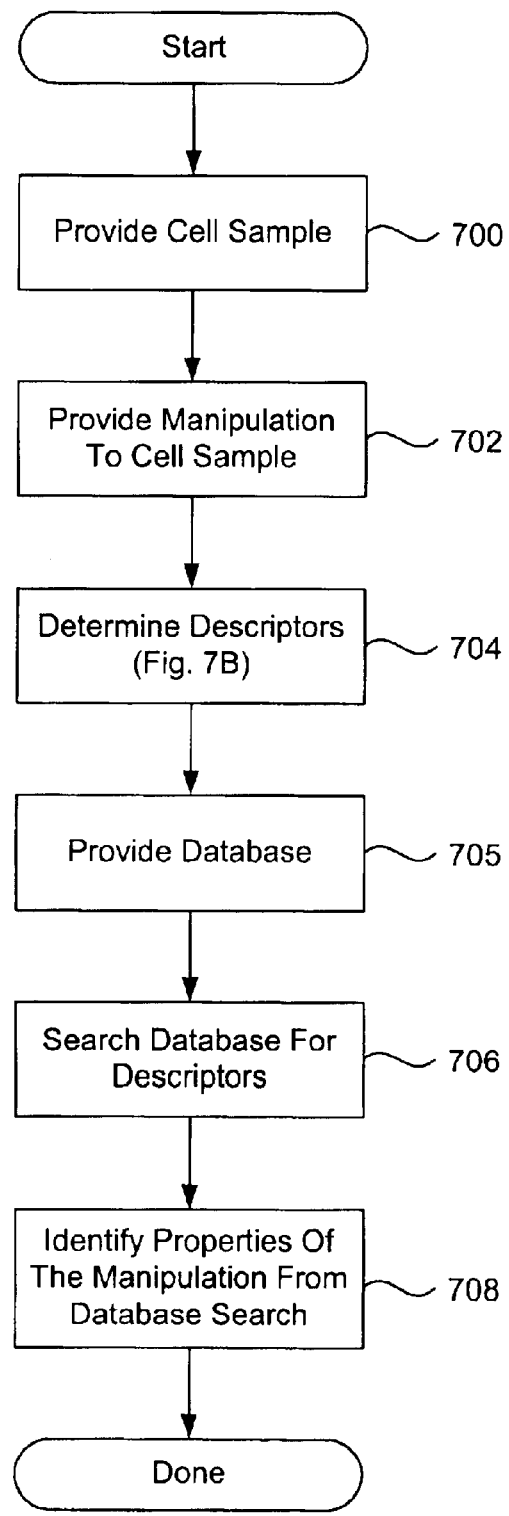
FIG. 7A illustrates a representative block flow diagram of simplified process steps of a method for determining properties of a manipulation based upon effects of the manipulation on one or more portions of one or more cells in a particular embodiment according to the present invention.

FIG. 7A illustrates a representative block flow diagram of simplified process steps of a method for determining properties of a manipulation based upon effects of the manipulation on one or more portions of one or more cells in a particular embodiment according to the present invention. This diagram is merely an illustration and should not limit the scope of the claims herein. One of ordinary skill in the art would recognize other variations, modifications, and alternatives. In step 700, one or more samples of cells can be provided. These cells can be live, dead, or fixed cells, or cell fractions. The cells also can be in one of many cell cycle stages, including G0, G1, S, G2 or M phase, M phase including the following cell cycle stages: interphase, prophase, prometaphase, metaphase, anaphase, and telophase.

Then, in a step 702, one or more samples of the manipulation can be provided to the cells. Manipulations can comprise one or any combination of chemical, biological, mechanical, thermal, electromagnetic, gravitational, nuclear, or temporal factors, for example. For example, manipulations could include exposure to chemical compounds, including compounds of known biological activity such as therapeutics or drugs, or also compounds of unknown biological activity. Or exposure to biologics that may or may not be used as drugs such as hormones, growth factors, antibodies, or extracellular matrix components. Or exposure to biologics such as infective materials such as viruses that may be naturally occurring viruses or viruses engineered to express exogenous genes at various levels. Bioengineered viruses are one example of manipulations via gene transfer. Other means of gene transfer are well known in the art and include but are not limited to electroporation, calcium phosphate precipitation, and lipid-based transfection. Manipulations could also include delivery of antisense polynucleotides by similar means as gene transfection. Other genetic manipulations include gene knock-outs or gene mutations. Manipulations also could include cell fusion. Physical manipulations could include exposing cells to shear stress under different rates of fluid flow, exposure of cells to different temperatures, exposure of cells to vacuum or positive pressure, or exposure of cells to sonication. Manipulations could also include applying centrifugal force. Manipulations could also include changes in gravitational force, including sub-gravitation (the preferred embodiment in outerspace). Manipulations could include application of a constant or pulsed electrical current. Manipulations could also include irradiation. Manipulations could also include photobleaching which in some embodiments may include prior addition of a substance that would specifically mark areas to be photobleached by subsequent light exposure. In addition, these types of manipulations may be varied as to time of exposure, or cells could be subjected to multiple manipulations in various combinations and orders of addition. Of course, the type of manipulation used depends upon the application.

Then, in a step 704, one or more descriptors of a state in the portions of the cells in the presence of the manipulation can be determined using the images collected on the imaging system. Descriptors can comprise scalar or vector values, representing quantities such as area, perimeter, dimensions, intensity, gray level, aspect ratios, and the like. Other types of descriptors include, but are not limited to, one or any combination of characteristics such as a cell count, an area, a perimeter, a length, a breadth, a fiber length, a fiber breadth, a shape factor, a elliptical form factor, an inner radius, an outer radius, a mean radius, an equivalent radius, an equivalent sphere volume, an equivalent prolate volume, an equivalent oblate volume, an equivalent sphere surface area, an average intensity, a total intensity, and an optical density. These descriptors can be average or standard deviation values, or frequency statistics from the descriptors collected across a population of cells. These descriptors can be further reduced using other methods such as principal component analysis and the like. In some embodiments, the descriptors include features from different cell portions or cell types. That is, a first feature can be from a nuclei and a second feature is from another cell structure such as Golgi apparatus, mitochondria, spacing between cell structures or cells themselves, as well as many others.

Then, in a step 705, a database of cell information can be provided. Next, in a step 706, a plurality of descriptors can be searched from a database of cell information in order to locate descriptors based upon one of the descriptors of the manipulation. Then, in a step 708, properties of the manipulation are predicted based upon the properties of the located descriptors. Properties can comprise toxicity, specificity against a subset of tumors, mechanisms of chemical activity, mechanisms of biological activity, structure, adverse biological effects, biological pathways, clinical effects, cellular availability, pharmacological availability, pharmacodynamic properties, clinical uses and indications, pharmacological properties, such as absorption, excretion, distribution, metabolism and the like.

In a particular embodiment, step 706 comprises determining matching descriptors in the database corresponding to a prior administration of the manipulation to the descriptors of the present administration of the manipulation. In a particular embodiment according to the present invention, combinations of measurements of scalar values can provide predictive information. A database can be provided having one or more "cellular fingerprints" comprised of descriptors of cell-substance interactions of drugs having known mechanisms of action with cells. Such descriptors can be analyzed, classified, and compared using a plurality of techniques, such as statistical classification and clustering, heuristic classification techniques, a technique of creating "phylogenetic trees" based on various distance measures between descriptors from various drugs. In this embodiment, numeric values for the descriptors can be used by comparison techniques. A phylogenetic tree can be created that illustrates a statistical significance of the similarity between descriptors for the drugs in the database. Because the drugs used to build the initial database are of known mechanism, it can be determined whether a particular scalar value in a descriptor is statistically predictive. Finally, a compound descriptor with no known mechanism of action can be queried against the database and be statistically compared and classified among the drugs in the database that the compound most resembles.

In a particular embodiment, relationships between measured morphological properties of images and physiological conditions can be determined. Relationships can include, for example, treatment of different cell lines with chemical compounds, or comparing cells from a patient with control cells, and the like. In a presently preferable embodiment, comparisons can be performed on acquired image features. Some embodiments can comprise statistical and neural network—based approaches to perform comparisons of various features. The foregoing is provided as merely an example, and is not intended to limit the scope of the present invention. Other techniques can be included for different types of data.

In some embodiments, classification, clustering and other types of predictive data analysis can be performed on features extracted from cell images. In a presently preferable embodiment, statistical procedures for comparisons, classification and clustering are performed on data obtained from imaging cells.

Fragments of data preparation and pre-formatting (S language):

```
>tmp.frame <- Generic.Summary
>names1 <- paste("Cell.line.5", tmp.names, sep = ".")
>by.compound.matrix <- as.matrix(arranged.by.compound)
```

Example of the code for principal component analysis (data preparation) using S language:

```
all.data.princomp <- menuPrincomp(data =
by.compound.matrix, scores = T, cor = "Correlation",
na.action = T, print.short = T, print.importance = T,
print.loadings = T, cutoff.loadings = 0.1, plot.screeplot
= T, plot.loadings = T, plot.biplot = T,
plot.biplot.choices = c(1,2), predict.p = F)
```

Example of clustering using a divisive hierarchical clustering algorithm:

```
> div.hier.2.manhattean.cluster$call
diana(x = tmp.sum.by.comp, diss = F, metric =
"manhattan",
    stand = T, save.x = T, save.diss = T
```

Another embodiment utilizes existing tools for biological sequence similarity searches, classification, and phylogenetic analysis. In a particular embodiment, numbers in a numerical descriptor can be substituted by one or more of nucleic acid or amino acid codes according to a one of several sets of rules. Once converted into a corresponding nucleotide or amino acid sequence representation, the fingerprints can be analyzed and compared using software and algorithms known in the art for genetic and peptide sequence comparisons, such as GCG, a product of Genetics Computer Group, with company headquarters in Madison Wis. Select embodiments comprising such approaches enable the use of a broad array of sophisticated algorithms to compare, analyze, and cluster gene and protein sequences. Many programs performing this task are known to those of ordinary skill in the art, such as for example, the PHYLIP (PHYlogeny Interference Package) a package of programs for inferring phylogenies (evolutionary trees) described in (Feldenstein, J. 1996 Methods Enzymol 266:418–427 and Feldenstein, J. 1981 J. Mol. Evol. 17(6):368–376).

Embodiments can perform such analysis based upon factors such as numerical value, statistical properties, relationships with other values, and the like. Further details of a step of manipulation are noted more particular below.

Figure 7B:
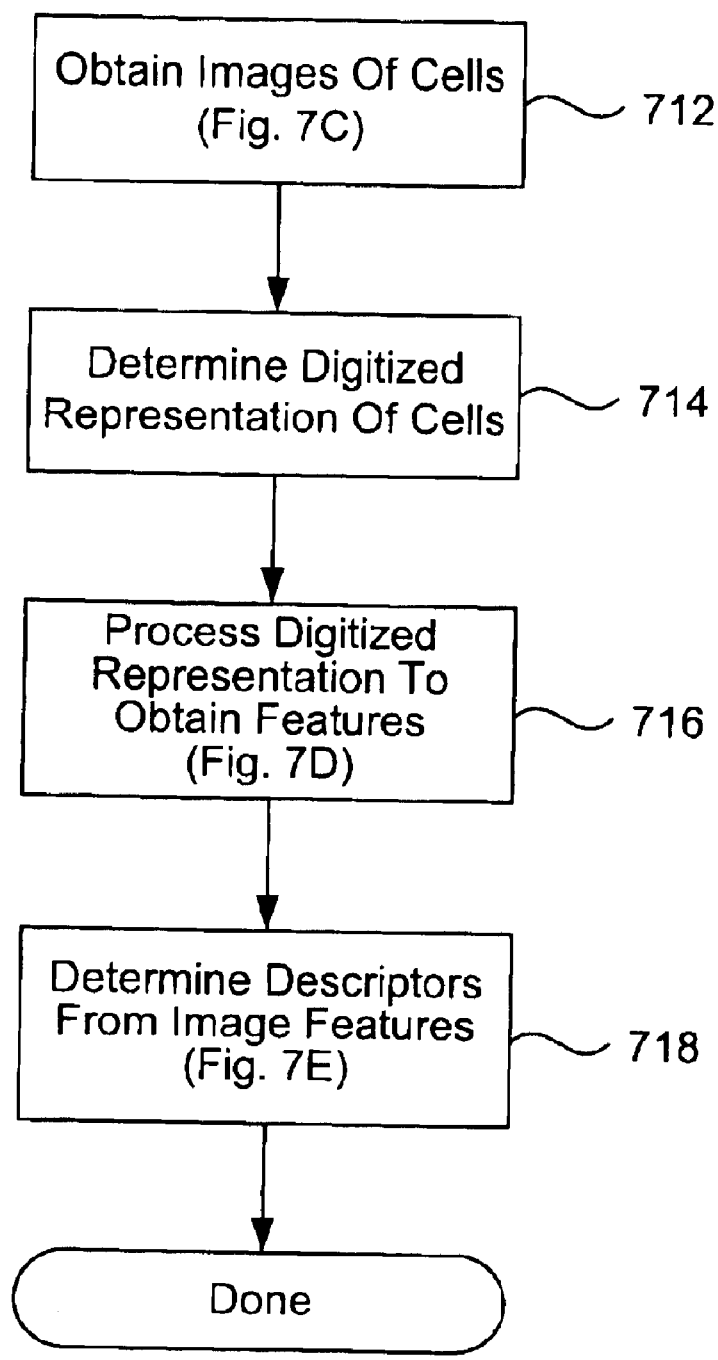
FIG. 7B illustrates a representative block flow diagram of simplified process steps for determining one or more descriptors of a state in the portions of the cells in the presence of the manipulation of step 704 of FIG. 7A in a particular embodiment according to the present invention.

FIG. 7B illustrates a representative block flow diagram of simplified process steps for determining one or more descriptors of a state in the portions of the cells in the presence of the manipulation of step 704 of FIG. 7A in a particular embodiment according to the present invention. This diagram is merely an illustration and should not limit the scope of the claims herein. One of ordinary skill in the art would recognize other variations, modifications, and alternatives. In a step 712, an image of a cell portion is obtained. In some embodiments, the cell portion is visualized with a fluorescently labeled marker which is specific for the portion or portions of interest. A cell portion can include, for example, one or more of the following: nuclei, golgi apparatus, and other features. The cell portion may vary in select embodiments according to the invention. Then, in a step 714, a digitized representation of the image obtained in step 712 is determined. In some embodiments, steps 714 and step 712 can comprise a single step. These embodiments use a digital imaging means such as a digital camera, to obtain a digital image of the target directly. Next, in a step 716, the digital representation of the image is processed to obtain image features. Image features can include such quantities as area, perimeter, dimensions, intensity, aspect ratios, and the like. Then, in a step 718 descriptors can be determined from the image features. Descriptors can comprise scalar or vector quantities and can comprise the image features themselves, as well as composed features, such as shape factor derived by a relationship $4\pi^*$ area/perimeter, and the like. Descriptors can also comprise statistical quantities relating to feature characteristics across a population of cells, such as a standard deviation, and average, and the like.

In a preferred embodiment, cells can be placed onto a microscope, such as a Zeiss microscope, or its equivalent as known in the art. A starting point, named Site A01, is identified to the microscope. A plurality of exposure parameters can be optimized for automated image collection and analysis. The microscope can automatically move to a new well, automatically focus, collect one or more images, at one or more wavelengths, move to a next well, and repeat this process for all designated wells in a multiple well plate and for multiple plates. A file having a size and an intensity distribution measurement for each color and rank for each well can then be created for the images acquired. Based on this information, a user or a computer can revisit sites of interest to collect more data, if desired, or to verify automated analysis. In a presently preferred embodiment, image automatic focus and acquisition can be done using computer software controlling the internal Z-motor of the microscope. Images are taken using a 10×, 20×, or 40× air long working distance objectives. Sometimes multiple images are collected per well. Image exposure times can be optimized for each fluorescent marker and cell line. The same exposure time can be used for each cell line and fluorescent marker to acquire data.

Figure 7C:
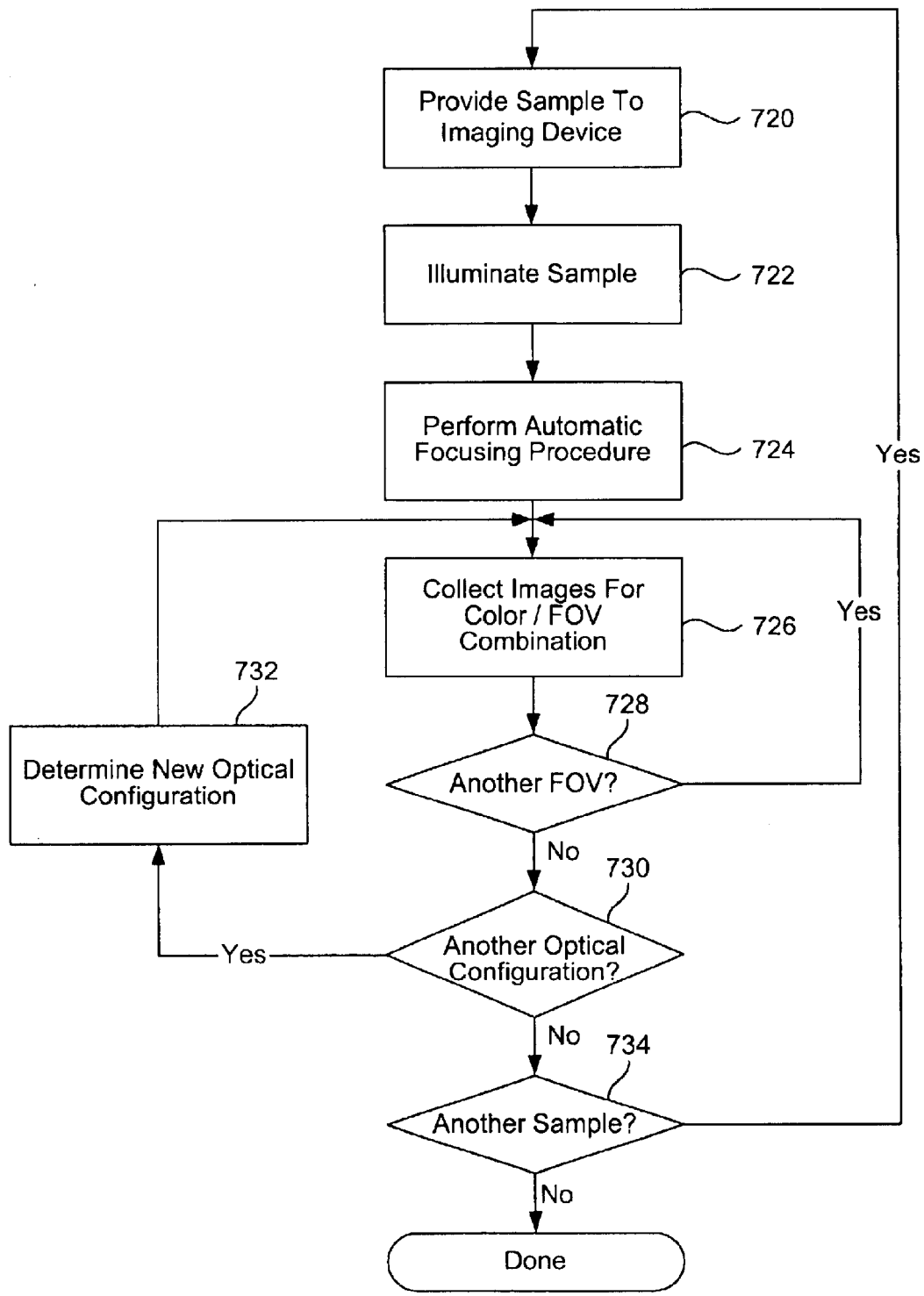
FIG. 7C illustrates a representative block flow diagram of simplified process steps for obtaining images of cell portions of step 712 of FIG. 7B in a particular embodiment according to the present invention.

FIG. 7C illustrates a representative block flow diagram of simplified process steps for obtaining images of cell portions of step 712 of FIG. 7B in a particular embodiment according to the present invention. This diagram is merely an illustration and should not limit the scope of the claims herein. One of ordinary skill in the art would recognize other variations, modifications, and alternatives. The method is generally outlined by the steps below:

(1). In a step 720, a sample is provided to the imaging device. Samples can be provided in 96 well plates and the like. The sample may be loaded into a microscope, such as a Zeiss microscope or equivalent. Part of this process may involve placing a plate onto an imaging stage and reading a bar code.

(2). In a step 722, a set of optical filters is selected to shine light of the appropriate wavelength to illuminate the first sample, which may be contained in a first well designated A01.

(3). In a step 724, an automatic focusing procedure is performed for the site. In a particular embodiment, the internal z-motor of the microscope which is attached to the objective nosepiece is used for automatic focusing of the microscope. In an alternative embodiments, the plate holding the samples is moved to perform automatic focusing of the microscope, or focusing can be performed by moving optical components attached to the microscope and the like.

(4). In a step 726, images are collected for the site. Images can be collected for every color at every site. Present embodiments can provide images for up to four colors. However, embodiments are contemplated that can provide more colors by using either a monochromator coupled with excitation filters which are on a filter wheel, or by digitally separating overlapping fluorophores. Those knowledgeable in the field will know that given calibration images of single fluorophores, a look-up table can be devised which will allow for the digital removal of fluorescence bleed-though of fluorescence which may occur in optical channels other than the one for which that filter has been optimized in instances of using more than one fluorophore at once. Cell growth and density information is also collected. Cell density is determined by what percentage of the area being imaged is inhabited by cells. In some embodiments, imaging can be facilitated using one or more biosensors, molecules such as non-proteins, i.e., lipids and the like, that are luminscently tagged. However, some embodiments can also use fluorescence polarization and the like. Fluorescence polarization is a homogeneous fluorescence technology where the excited state of the molecule lasts much longer than in normal fluorescence, taking seconds to minutes to reach equilibrium, obliterating the need to wash away fluorescence markers that are not specifically bound to a marker. Further, embodiments can detect differences in spectral shifts of luminescent markers. Some fluorescence markers, such as Nile Red sold by Molecular Probes of Eugene, Oreg., will change its emission peak wavelength depending on its environment. One can detect these changes by monitoring the level of fluorescence at both wavelengths and reading out at ratio of the two.

(5). In a step 728, a determination is made whether more fields of view need to be taken for a particular color. If this is so, then processing continues at step 726 at a new site. Otherwise, processing continues with a decisional step 730. Images can now be taken by repeating step 726. In a preferred embodiment 4 to 9 images are collected at each site.

(5). In a step 730, a determination is made whether more optical configurations need to be taken in order to obtain images for all differently-marked cell portions the sample. If this is so, then in a step 732 a new optical configuration is determined. Images for the new optical configuration can now be taken by repeating steps 726 and 728.

(6). In a decisional step 734, after all optical configurations and images for fields of view in a sample have been obtained, a determination is made whether any further samples remain to be analyzed. If so, a new sample is brought into view and processing continues with step 720. Otherwise, image processing is complete. In a presently preferable embodiment, image data can be stored on a CD ROM using a CD ROM burner, such as CRW4416 made by Yamaha of Japan. However, other mass storage media can also be used.

Figure 7D:
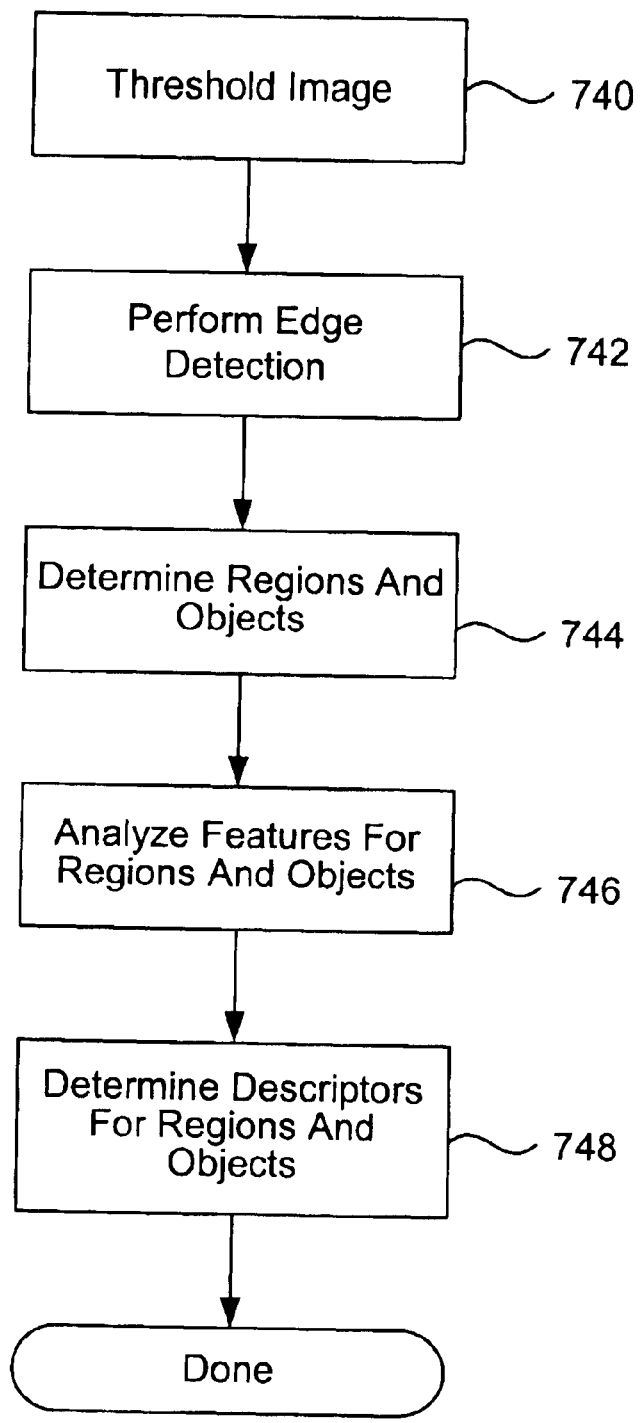
FIG. 7D illustrates a representative block flow diagram of simplified process steps for processing digitized representations of step 716 of FIG. 7B in a particular embodiment according to the present invention.

FIG. 7D illustrates a representative block flow diagram of simplified process steps for processing digitized representations of step 716 of FIG. 7B in a particular embodiment according to the present invention. This diagram is merely an illustration and should not limit the scope of the claims herein. One of ordinary skill in the art would recognize other variations, modifications, and alternatives. The method is generally outlined by the steps below:

(1). In a step 740, a digitized image input is preprocessed. Preprocessing might include, but is not limited to, such operations as background subtraction, thresholding, smoothing, adoptive filtering, edge enhancements, contrast enhancements, histogram equalization. A particular combination of preprocessing steps can be applied to images in successive steps or in parallel to copies of the image.

A simplified example of a smoothing and background subtraction procedure in a MatLab language is presented in computer code below:

```
function Isubtracted = cmBackgrSubtr1(I,k)
% cmBackgrSubtr1(I, k) simple flat backround (=modal*k) subtraction
% Y = cmBackgrSubtr1(I,k) – image Y is generated by
% subtraction (with saturation) of modal pixel value of I
multiplied by k
% DEFAULT – k=1
if (nargin == 1)
    k=1;
end
if (size(k)~=1)
    error('cmBackgrSubtr1: parameter k should be a number.
Exiting . . . ');
end
%modpixnum = floor(size(I(:),1)/2);
%sortedval = sort ( double(I(:)) );
%modpixel = sortedval (modpixnum);
modpixel = median(double(I(:)));
bg = k*modpixel;
Isubtracted = mmsubm( uint8(I), uint8(round(ones(
    size(I))*k*modpixel )) );
```

An example of a procedure for thresholding in computer code (MatLab) is presented below:

```
function thresh = GetThreshByPeriml(I, M)
% GetThreshByPeriml (I) Finds optimal thresholding value for
image I
% N = GetThreshByPeriml (I) Finds thresholding value N for
image I
% N = GetThreshByPeriml (I, M) tests threshold values up to
M
% DEFAULT M = maximum pixel value in I
% note that GetThreshByArea is significantly faster
% finds a threshold value that causes the maximal change in
the
% total perimeter of the objects (Russ ????)
% see Matlab_Auto_threshold1_1-23-99.doc for more details
% Note: works somewhat better on SMOOTH images (i.e.
medfilt2(I, [3 3]) two times
if (nargin == 0)
    error (strcat( mfilename,' : at least one parameter
required'));
elseif (nargin == 1)
    M = double(max(I(:))); %test thresholds up to maximum
pixel value in I
elseif (nargin > 2)
    error (strcat (mfilename,' too many parameters'));
end
if (size(M) >1)
    error (strcat(mfilename, ' : argument M should be a
number'));
end
Minval = double( min(I(:)));
step = 1;
%generate vertical vector perims with total perimeters of
objects at different
%threshold values
for i=Minval : step : M
    bwI = im2bw(I, i/255);
    prI = bwperim(bwI);
    pr = sum(prI(:));
    if (exist('perims', 'var') == 0) %perims is yet
undefined
        perims = pr;
    else
        perims = cat(1, perims, pr);
    end
end
% vector prdiffs contains differences between successive
perimeters
prdiffs = diff(perims);
mindecrease = min(prdiffs);
minvalues = find(prdiffs == mindecrease);
index_of_mindecrease = minvalues(1);
thresh = index_of_mindecrease + 1;
% ===============end GetThresh1==============
```

Thresholding provides a specific intensity, such that pixels darker than the threshold are deemed black, and pixels lighter than the threshold are considered white. The thresholded image can be processed using binary image processing techniques in order to extract regions.

(2). In a step 742+744, the digitized image input is subjected to object identification. This can be accomplished by a variety of procedures, for example by thresholding or edge detection and subsequent morphological opening and closing. Edge detection can be accomplished by means of gradient-based or zero-crossing methods, such as Sobel, Canny, Laplassian, Perwitt, and other methods.

An example of object identification procedure based on Canny edge detection (in MatLab language) is presented below:

```
function Imask = cmMaskDNA1(I);
% cmMaskDNA1 - generates binary mask for cell nuclei through
edge de#ection
% Imask cmMaskDNA1(I)
% PARAMETERS
% I - intensity image (grayscale)
% OUTPUT
% Imask - BW image with objects from I
%
% For more details see Notebook Matlab_DNA_masking1_1-22-
99.doc
% Uses SDC Morphology Toolbox V0.7
if (nargin ~= 1)
    error ('Wrong number of input parameters');
end
if (nargout ~= 1)
    error('Wrong number of output parameters: one output
argument should be provided');
end
Imask = edge(I, 'canny');
Imask = mmdil (Imask, mmsecross(1))
Imask = mmero ( mmclohole(Imask,mmsecross(1)));
Imask = mmedgeoff(Imask, mmsecross(1));
% note that mmedgeoff this command removed FILLED OBJECTS
but not touching OUTLINES.
% these outlines can be removed by filtering:
Imask = medfilt2 (Imask, [5 5]);
%=========end cmMaskDNA1 =====================
```

However, embodiments can also use other techniques, such as Fast Fourier Transforms (FFT) and the like as known in the art without departing from the scope of the present invention.

(4). In a step 746, a plurality of region features can be determined. For example, in a representative embodiment, image features can include such quantities as area, perimeter, dimensions, intensity, aspect ratios, and the like. Features not directly related to individual objects are also being extracted.

An example of a procedure for extraction of some of the features (MatLab language) is presented below:

```
function OData = cmGetObjectsData(I, Ilabel)
% cmGetObjectsData returns array measurements of objects in
image "I" masked by "Ilabel"
% EV 2-3-99; 2-10-99
% OData = cmGetObjectsData(I, Ilabel) returns an array of
morphological and intensity measurements
% taken from a grayscale image "I". Objects are identified
on a mask image Ilabel, usually
% created by bwlabel()
% OUTPUT:
% Each row in the output array OData represents individual
object
% columns contain the following measurements:
%
% 1 - Index ("number" of an object);      8 - Solidity;
% 2 - X coordinate of the center of mass; 9 - Extent;
% 3 - Y coordinate          -"-    ;      10 - Total
Intensity;
% 4 - Total Area (in pixels);             11 - Avg. Intensity;
% 5 - Ratio of MajorAxis/MinorAxis;       12 - Median
Intensity;
% 6 - Eccentrisity;                       13 - Intensity of 20%
bright - pixel
% 7 - EquivDiameter;                      14 - Intensity of 80%
bright pixel
%
% For details on morphological parameters see information on
MatLab imfeature ();
% Intensity parameters are either obvious or are documented
in comments in this file.
if (nargin ~= 2)
    error ('function requires exactly 2 parameters');
end
```

```
    if (nargout ~= 1)
        error ('function has 1 output argument (array X by 14)');
    end
% finished checking arguments
% first collect morphological parameters in a structure
array:
ImStats = imfeature(Ilabel, 'Area', 'Centroid',
'MajorAxisLength', ...
        'MinorAxisLength', 'Eccentricity', 'EquivDiameter', ...
        'Solidity', 'Extent', 8 );
% now convert it into array (matrix) while collecting
intensity data for each object:
%preallocate output array:
numobjects = size(ImStats, 1);
OData = zeros(numobjects, 14);
%now convert ImStats into array and add intensity data to it
for k=1:numobjects
    OData(k, 1) = k;
    OData(k, 2) = ImStats(k).Centroid(1);
    OData(k, 3) = ImStats(k).Centroid(2);
    OData(k, 4) = ImStats(k).Area;
    OData(k, 5) = (ImStats(k).MajorAxisLength) /
(ImStats(k).MinorAxisLength);
    OData(k, 6) = ImStats(k).Eccentricity;
    OData(k, 7) = ImStats(k).EquivDiameter;
    OData(k, 8) = ImStats(k).Solidity;
    OData(k, 9) = ImStats(k).Extent;
    % now collect and assign intensity parameters from image
I
    object_pixels = find( Ilabel == k);
    object_area = size(object_pixels, 1); %same as total
number of pixels in the object
    object_intensities = double(I(object_pixels)); % need to
convert to double to do math
    sorted_intensities = sort (object_intensities); % will
need to get median, 20% and 80% pixels
    total_intensity = sum(object_intensities, 1);
    avg_intensity = total_intensity / object_area;
    median_intensity = sorted_intensities( floor(
object_area/2 ) + 1);
    pix20 = sorted_intensities( floor(object_area*0.2)+1 ) ;
%brightest pixel among dimmest 20%
    pix80 = sorted_intensities( floor(object_area*0.8)+1 ) ;
    OData(k, 10) = total_intensity;
    OData(k, 11) = avg_intensity;
    OData(k, 12) = median_intensity;
    OData(k, 13) = pix20; %brightest pixel among dimmest 20%
    OData(k, 14) = pix80; %dimmest pixel among brightest 20%
end %for
%=================== end function
cmGetObjectsData () ===================
```

(5). In a step 748, quantitative descriptors, characterizing cell state are calculated based on the feature measurements extracted at step 746. For example, histogram distribution of intensities of cell nuclei provides information about the population cell cycle stages.

In a particular embodiment according to the present invention, data analysis techniques for describing the fluorescence patterns of cell portions in multiple cell lines in the presence and absence of compounds are provided. Automated image analysis techniques can include determining one or more regions from around nuclei, individual cells, organelles, and the like, called "objects" using a thresholding function. Objects that reside on the edge of an image can be included or excluded in various embodiments. An average population information about an object can be determined and recorded into a database, which can comprise a database text file or Excel spreadsheet, for example. However, embodiments can use any recording means without departing from the scope of the present invention. Values measured can be compared to the visual image. One or more types of numerical descriptors can be generated from the values. For example, descriptors such as a number of objects, an average, a standard deviation of objects, a histogram (number or percentage of objects per bin, average, standard deviation), and the like can be determined.

In a particular embodiment according to the present invention, data can be analyzed using morphometric values derived from any of a plurality of techniques commonly known in the art. Fluorescent images can be described by numerical values, such as for example, an area, a fluorescence intensity, a population count, a radial dispersion, a perimeter, a length, and the like. Further, other values can be derived from such measurements. For example, a shape factor can be derived according to a relationship $4\pi *$ area/perimeter. Other values can be used in various embodiments according to the present invention. Such values can be analyzed as average values and frequency distributions from a population of individual cells.

In a particular embodiment according to the present invention, techniques for the automatic identification of mitotic cells are provided. Image analysis techniques employing techniques such as multidimensional representations, frequency-based representations, multidimensional cluster analysis techniques and the like can be included in various embodiments without departing from the scope of the present invention. Techniques for performing such analyses are known in the art and include those embodied in MatLab software, produced by Math Works, a company with headquarters in Natick, Mass.

Figure 7E:
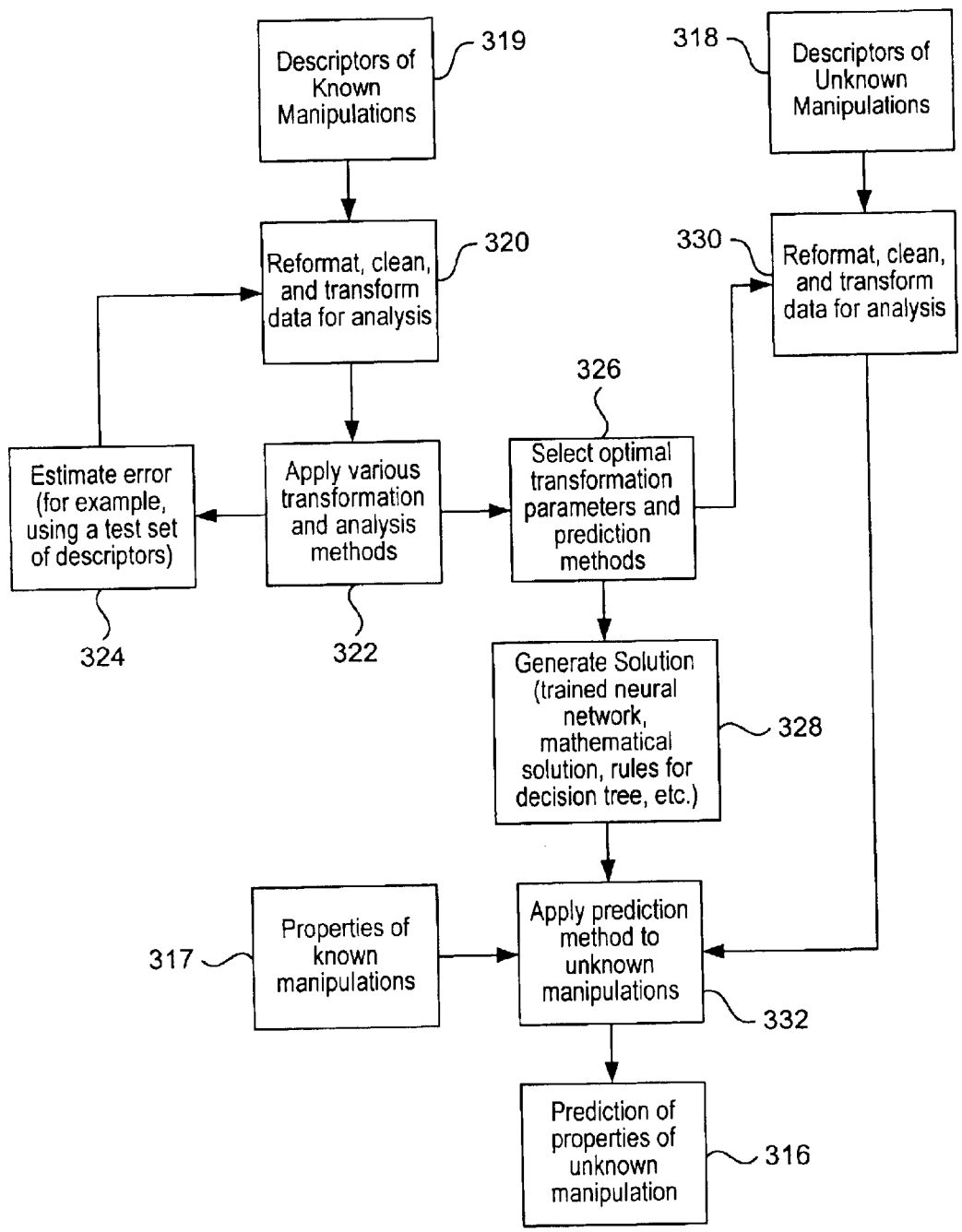
FIG. 7E illustrates a representative block flow diagram of simplified process steps for analyzing image feature values to obtain descriptors of cell state of step 718 of FIG. 7B in a particular embodiment according to the present invention.

Scalar values providing efficacious descriptors of cell images can be identified using the techniques of the present invention to perform predictive analysis of drug behavior. In a presently preferred embodiment, a plurality of heterogeneous scalar values can be combined to provide descriptors for each manipulation. By applying predictive analysis routines to the collections of these descriptors, predictive information about any number of manipulations and cell interactions can be extracted. FIG. 7E illustrates a representative block flow diagram of simplified process steps for analyzing image feature values to obtain descriptors of cell state of step 718 of FIG. 7B in a particular embodiment according to the present invention. This diagram is merely an illustration and should not limit the scope of the claims herein. One of ordinary skill in the art would recognize other variations, modifications, and alternatives. FIG. 7E illustrates an input data of descriptors of known manipulations 319. A step 320 of reformatting and transforming data 319 to formats suitable for analysis is performed. Additionally, a "cleaning" process can eliminate outlying data points and the like in the data. Then, in a step 322, a decision is made whether to continue with step 324 or with step 326 based upon determining a particular type of analysis appropriate for the present application or particular type of prediction. If decisional step 322 determines processing should continue with step 324, then, in that step, an error estimate using a set of test descriptors is performed to estimate the quality of a prediction and processing continues with step 320. Once an optimal prediction is achieved, processing continues with step 326. In step 326, optimal transformation parameters and prediction methods are selected for use in steps 328 and 330 which analyze data about an unknown manipulation. In a step 328, a solution is generated based upon any of techniques including training a neural network, solving a mathematical equation, applying decision tree rules and/or the like. In a step 330, an input data set of unknown descriptors 318 is reformatted and transformed based upon the optimal transformation parameters selected in step 326 using the transformation procedures in steps 320, 322 and 324. In a step 332, predictions techniques are applied to the reformatted manipulations from step 330 and the solution generated in step 328 and a plurality of properties of known manipulations 317 (e.g., therapeutic properties, and the like) in order to determine a prediction of properties of unknown manipulation 316.

Figure 7F:
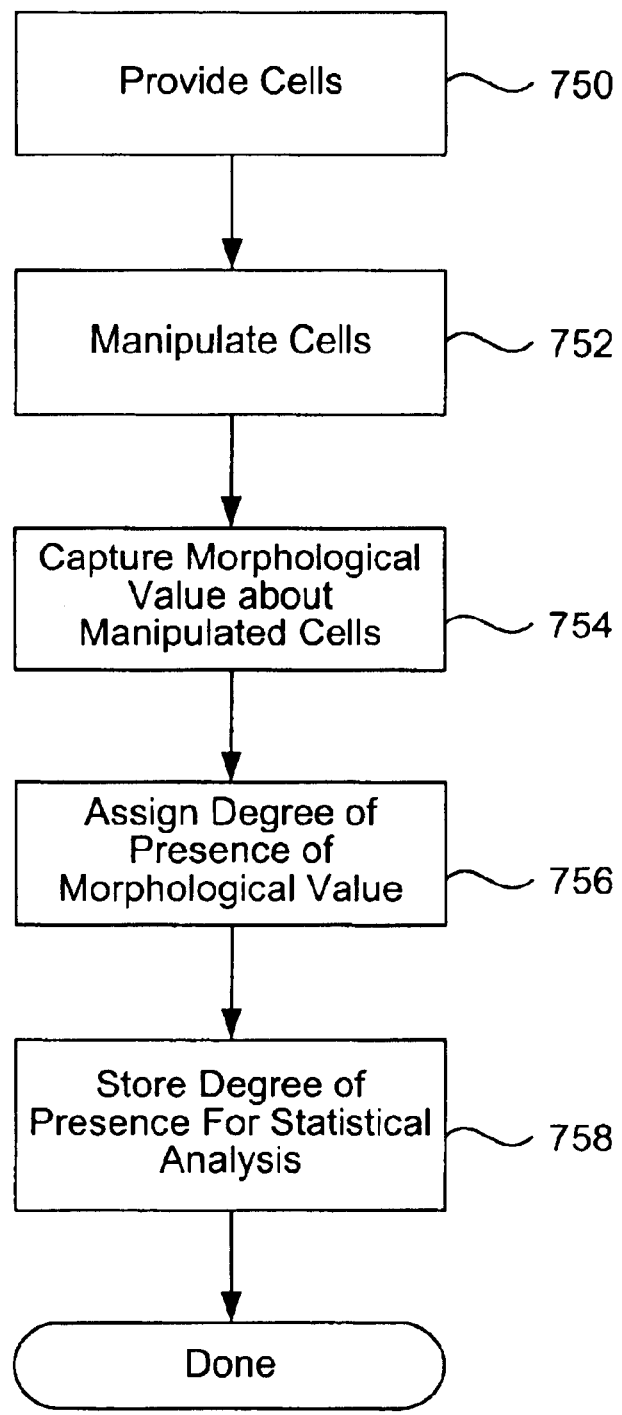
FIG. 7F illustrates a representative block flow diagram of simplified process steps for a method of mapping a manipulation of cells to a physiological characteristic in a particular embodiment according to the present invention.

FIG. 7F illustrates a representative block flow diagram of simplified process steps for a method of mapping a manipulation of cells to a physiological characteristic in a particular embodiment according to the present invention. This diagram is merely an illustration and should not limit the scope of the claims herein. One of ordinary skill in the art would recognize other variations, modifications, and alternatives. The method is generally outlined by the steps below:

(1) In a step 750, a plurality of cells, e.g., dead, live, cell fractions or mixtures of cells are provided.

(2) Then, in a step 752, the plurality of cells is manipulated, where manipulation occurs using a source (s) from one or a combination selected from an electromagnetic, electrical, chemical, thermal, gravitational, nuclear, temporal, or a biological source.

(3) Next, in a step 754, a feature value is captured from the plurality of cells. The feature value can include one or any combination of characteristics such as cell count, area, perimeter, length, breadth, fiber length, fiber breadth, shape factor, elliptical form factor, inner radius, outer radius, mean radius, equivalent radius, equivalent sphere volume, equivalent prolate volume, equivalent oblate volume, equivalent sphere surface area, average intensity, total intensity, and optical density. This list is not meant to be limiting.

(4) Then, in a step 756, a degree of presence of one or more feature values arc assigned for each manipulation.

(5) In a step 758, the feature values from the plurality of cells are stored in memory locations. From the memory locations the values can be used for statistical analyses to produce predictive information about the relatedness of the descriptors of the manipulations to one another. This information is used to infer properties of the manipulations.

Figure 7G:
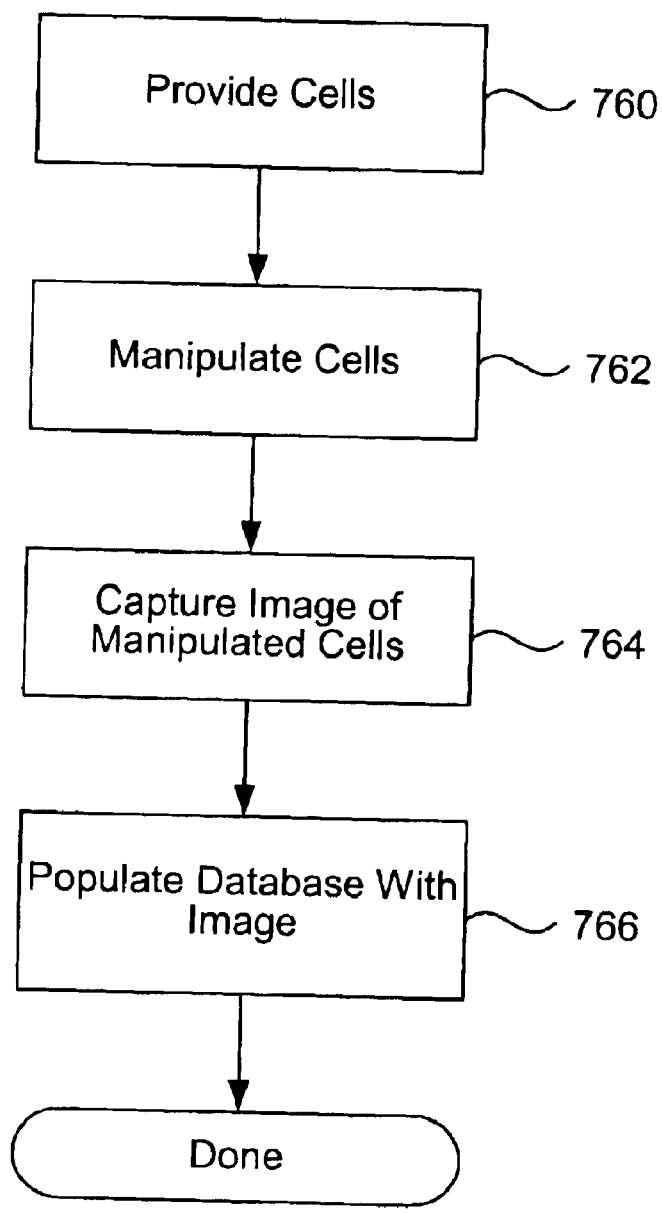
FIG. 7G illustrates a representative block flow diagram of a simplified process steps for a method for populating a database with manipulated biological cell information in a particular embodiment according to the present invention.

FIG. 7G illustrates a representative block flow diagram of a simplified process steps for a method for populating a database with manipulated biological cell information in a particular embodiment according to the present invention. This diagram is merely an illustration and should not limit the scope of the claims herein. One of ordinary skill in the art would recognize other variations, modifications, and alternatives. The method is generally outlined by the steps below:

(1) In a step 760, a plurality of cells in various stages of the cell cycle, such as for example, the stages of interphase, prophase, metaphase, anaphase, and telophase are provided.

(2) Then, in a step 762, each of the cells in the various stages of mitotic development is manipulated.

(3) Next, in a step 764, an image of the plurality of manipulated cells is captured using image acquisition techniques in order to provide a morphometric characteristic of each of the manipulated cells.

(4) In a step 766, an image database may be populated with the image of the plurality of manipulated cells.

Accordingly, the present invention provides a novel database design. In a particular embodiment according to the present invention, a method for providing a database comprises measurement of a potentially large number of features of one or more sub-cellular morphometric markers. Markers can be from any of a large variety of normal and transformed cell lines from sources such as for example, human beings, fungi, or other species. The markers can be chosen to cover many areas of cell biology, such as, for example markers comprising the cytoskeleton of a cell. The cytoskeleton is one of a plurality of components that determine a cell's architecture, or "cytoarchitecture". A cytoarchitecture comprises structures that can mediate most cellular processes, such as cell growth and division, for example. Because the cytoskeleton is a dynamic structure, it provides a constant indication of the processes occurring within the cell. The cytoarchitecture of a cell can be quantified to produce a one or more scalar values corresponding to many possible cellular markers, such as cytoskeleton, organelles, signaling molecules, adhesion molecules and the like. Such quantification can be performed in the presence and absence of drugs, peptides, proteins, anti-sense oligonucleotides, antibodies, genetic alterations and the like. Scalar values obtained from such quantification can provide information about the shape and metabolic state of the cell.

In a presently preferred embodiment, scalar values can comprise morphometric, frequency, multi-dimensional parameters and the like, extracted from one or more fluorescence images taken from a number of cellular markers from a population of cells. Two or more such scalar values extracted from a plurality of cell lines and markers grown in the same condition together comprise a unique "fingerprint" or descriptor that can be incorporated into a database. Such cellular descriptors will change in the presence of drugs, peptides, proteins, antisense oligonucleotides, antibodies or genetic alterations. Such changes can be sufficiently unique to permit a correlation to be drawn between similar descriptors. Such correlations can predict similar properties or characteristics with regard to mechanism of action, toxicity, animal model effectiveness, clinical trial effectiveness, patient responses and the like. In a presently preferred embodiment, a database can be built from a plurality of such descriptors from different cell lines, cellular markers, and compounds having known mechanisms of action (or structure, or gene response, or toxicity).

The present invention also provides database and descriptor comparisons according to other embodiments. In a particular embodiment according to the present invention, measurement of scalar values or features can provide predictive information. A database can be provided having one or more "cellular fingerprints" comprised of descriptors of cell substance interactions of drugs having known mechanisms of action with cells. Such descriptors can be compared using a plurality of techniques, such as a technique of creating "phylogenetic trees" of a statistical similarity between the descriptors from various drugs. In a present embodiment, scalar, numeric values can be converted into a nucleotide or amino acid letter. Once converted into a corresponding nucleotide representation, the descriptors can be analyzed and compared using software and algorithms known in the art for genetic and peptide sequence comparisons, such as GCG, a product of Genetics Computer Group, with company headquarters in Madison Wis. In an alternative embodiment, numeric values for the fingerprints can be used by comparison techniques. A phylogenetic tree can be created that illustrates a statistical significance of the similarity between descriptors for the drugs in the database. Because the drugs used to build the initial database are of known mechanism, it can be determined whether a particular scalar value in a descriptor is statistically predictive. Finally, a compound fingerprint with no known mechanism of action can be queried against the database and be statistically compared and classified among the drugs in the database that the compound most resembles.

In a particular embodiment, relationships between measured morphometric properties and features of images and physiological conditions can be determined. Relationships can include, for example, treatment of different cell lines with chemical compounds, or comparing cells from a patient with control cells, and the like. In a presently preferable embodiment, a clustering can be performed on acquired image descriptors. Some embodiments can comprise statistical and neural network—based approaches to perform clustering and comparisons of various descriptors. The foregoing is provided as merely an example, and is not intended to limit the scope of the present invention. Other techniques can be included for different types of data. In some embodiments, clustering and comparing can be performed on features extracted from cell images. In a presently preferable embodiment, procedures for comparisons and phylogenetic analysis of biological sequences can be applied to data obtained from imaging cells.

Select embodiments comprising such approaches enable the use of a broad array of sophisticated algorithms to compare, analyze, and cluster gene and protein sequences. Many programs performing this task are known to those of ordinary skill in the art, such as for example, the program Phylip, and other packages. However, select embodiments according to the present invention can comprise a technique of statistical classification, statistical clustering, distance based clustering, linear and non-linear regression analysis, self-organizing networks, and rule-based classification.

Embodiments can perform such analysis based upon factors such as numerical value, statistical properties, relationships with other values, and the like. In a particular embodiment, numbers in a numerical descriptor can be substituted by one or more of nucleic acid or amino acid codes. Resulting "pseudo-sequences" can be subjected to analysis by a sequence comparison and clustering program.

Other types of databases can also be provided according to other embodiments. The database includes details about the properties of a plurality of standard drugs. When the descriptor of a test compound is compared to the database, predictions about the properties of the test compound can be made using any known property of the other compounds in the database. For example, properties about a compound in the database could include structure, mechanism of action, clinical side effects, toxicity, specificity, gene expression, affinity, pharmacokinetics, and the like. The descriptor of a compound of unknown structure from a natural products library could be compared to the descriptors of compounds with known structure and the structure could be deduced from such a comparison. Similarly, such information could lead to better approaches to drug discovery research including target validation and compound analogizing, as well as pre-clinical animal modeling, clinical trial design, side effects, dose escalation, patient population and the like.

According to the present invention, databases can be integrated with and complementary to existing genomic databases. Differential genomic expression strategies can be used for drug discovery using database technology. In one particular embodiment, cell data and cellular response data can be associated with a genetic expression profile assay to form a single assay. Live cells expressing fluorescence markers can be treated with a drug, imaged and analyzed for morphometry; and then analyzed for mRNA for expression. Such embodiments can provide rapid development of tools to link cellular behavior with functional genomics.

Database methods according to the present invention can be used to predict gene function and to assist in target validation. Databases that include genetic diversity, i.e., having cellular descriptors from cells of differing genetic backgrounds (tumor, tissue specific, and gene knock out cell lines), can provide the capability to compare cells of unknown genetic background to those in the database. Similarly, the descriptor of an unknown cellular portion in the presence of multiple drugs can be queried against the descriptors of the known markers in the database. For example, if an unknown gene is tagged with Green Fluorescent Protein (GFP), the database may be used to identify the cellular portions for which that unknown gene encodes.

According to the present invention, target validation and specialized cell-based assay screening can be performed using database systems and methods to serve as a universal high-throughput cell-based assay that can evaluate the molecular mechanism of drug action. As new genes are isolated and identified, a large collection of available gene-based knowledge is becoming available. From this large collection of new genes, potential protein targets can be identified using the genomic tools of sequence analysis and expression profiling. However, unless a gene mutation is tightly linked to a disease state, further validation of individual targets is a time consuming process, becoming a bottleneck in drug discovery. Furthermore, robotics and miniaturization are making "High Throughput Screening (HTS)" the industry standard, substantially reducing the time and cost of running a target-based biochemical assay. Therefore, it is now possible to routinely screen large libraries and use a resulting "hit" to validate the target. In such approaches, a specialized cell-based assay would be developed to test hits for each target. Since this often involves the creation of cell lines expressing new markers, this stage may also become a bottleneck that cannot keep pace with HTS. In addition, these cell-based assays may not be amenable to high-throughput screening, making it difficult to test the increasing number of analogs arising from combinatorial chemistry.

In a particular embodiment according to the invention, a rapid characterization of large compound libraries for potential use as pharmaceutical products can be provided by predicting properties of compounds that relate to the compounds' potential as bioactive drugs. In many drug discovery situations, virtually millions of compounds can be passed through a HTS assay against a small number of validated targets. These assays produce hundreds to thousands of potential hits. These hits can then be subsequently screened by a pipeline of secondary and tertiary screens to further characterize their specificity, often time completely missing non-specific interactions with other proteins. Techniques according to the present invention can provide a replacement to such screening operations by providing information about cellular accessibility and mechanism of action for the hits coming from a HTS system. Furthermore, it can replace the biochemical FITS assay and allow rapid and accurate identification of attractive compounds from large libraries without an intervening biochemical assay. The cell information can be predictive of whether to continue into an animal model for each compound, and which animal model to pursue.

In some embodiments, techniques according to the present invention can provide tools for the later stages of drug development such as clinical trial design and patient management. The properties of known drugs, such as clinical trial and patient response information, will be used in a similar fashion as the pre-clinical information to provide predictions about the properties of novel compounds. Because the human cell is the locus of drug action, a database containing drug-cell interactions will be able to provide predictive value for this aspect of drug development.

Although the above has generally been described in terms of specific hardware, software, and methods, it is understood that many alternatives can exist. In particular, the present invention is not limited to a particular kind of data about a cell, but can be applied to virtually any cellular data where an understanding about the workings of the cell is desired. Thus, in some embodiments, the techniques of the present invention could provide information about many different types or groups of cells, substances, and genetic processes of all kinds. Of course, one of ordinary skill in the art would recognize other variations, modifications, and alternatives. Some examples according to the present invention are provided below.

EXPERIMENTS

To prove the principle and demonstrate the objects of the present invention, experiments have been performed to determine the effects of manipulations on cell structure using imaging and analysis techniques applied to a variety of situations. These experiments were performed by growing multiple cell lines in the presence of multiple compounds, or substances. Cells were fixed and stained with fluorescent antibodies or labels to multiple cellular portions. One or more images of the cells were then obtained using a digital camera. Descriptors were built by quantifying and/or qualifying patterns of one or more feature from each image in the cell lines under study. A database was built from the descriptors. As the database grows, it should be able to predict the mechanism of action of an unknown drug by comparing its effect with the effects of known compounds or to identify data clusters within large libraries of compounds.

In a first experiment, an automated method to count the number of cells and differentiate normal, mitotic, and apoptotic cells was created. Approximately, 5,000 HeLa cells were plated per well in a 96 well plate and grown for 3.5 days. The cells were fixed with −20° MEOH for 5 minutes, washed with TBS for 15 minutes, and then incubated in 5 mg/ml Hoechst 33342 in TBS for 15 minutes. Then, 72 images were collected with a 40× objective and 75 ms exposure time.

Figure 8A:
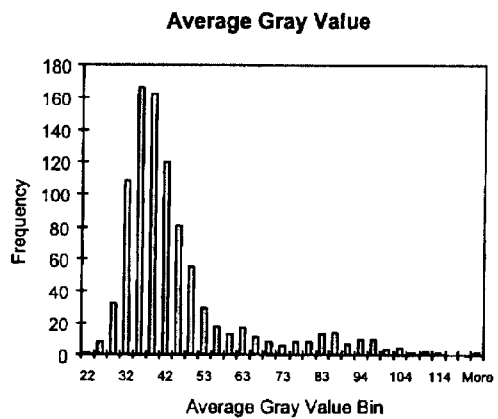
Figure 8B:
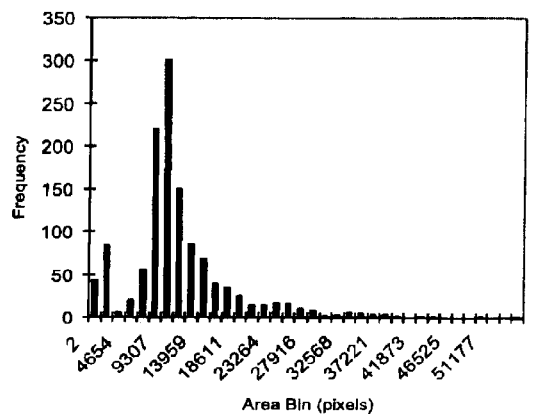

The analysis was performed on objects that met a certain size criteria that was based on 1) measuring the size of objects in the image that were clearly not cells and 2) excluding the first peak of the area histogram (FIG. 8B values 1-4654).

Figure 8C:
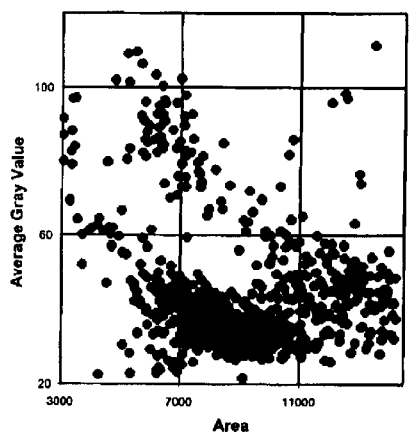
Figure 8D:
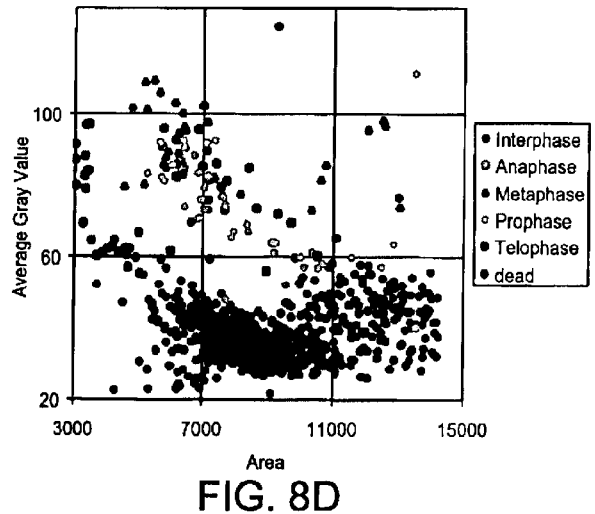
Figure 8E:
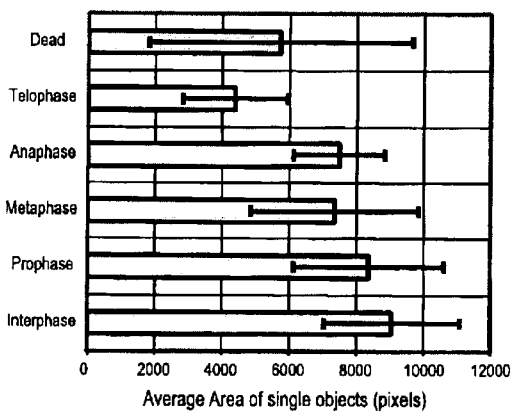
Figure 8F:
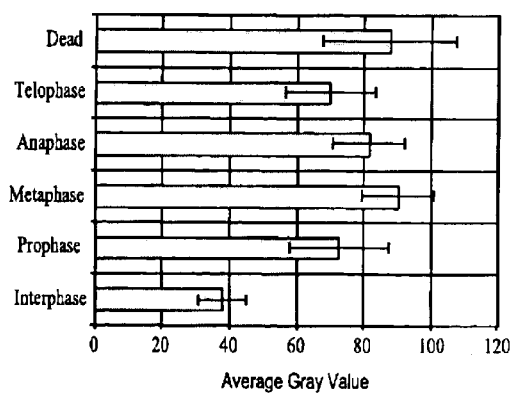

Histograms of the individual object data were generated for each type of feature. FIG. 8A shows the histogram for average intensity, and FIG. 8B shows histogram data for the area of each object. FIG. 8C shows the scatter plot of the average intensity vs. the area of all of the objects. The pattern of the scatter plot showed an interesting pattern: a large cluster of cells in one region of the graph, with a scattering of object points in other regions. Because mitotic structures are identified as particularly bright objects, most likely due to the biological fact that the chromatin is condensed, it seemed reasonable to go back to the original Hoechst images and the identify the cells which were either undergoing mitosis, or otherwise looked abnormal. Manual inspection of 917 cells resulted in the classification of each object. FIG. 8D shows a graph where each type of cellular classification is delimited. This graph clearly shows that the mitotic nuclei are exclusively brighter than the interphase nuclei. Further, the different phases of the cell cycle can be separated using these two features. FIGS. 8E–8F show bar graphs of the average and standard deviations of the areas and average intensities for each cell classification type. These graphs show that interphase nuclei are statistically less bright than mitotic nuclei and that telophase nuclei are statistically smaller than other mitotic nuclei.

Each image was thresholded to an intensity level of 20. A standard area value was set at 9500 pixels. Automated information gathering about all of the objects was done and collected into an Excel spreadsheet (for more information see, section on imaging system). The following information was recorded:

| IMAGE NAME | AVERAGE INTENSITY |
|---|---|
| OBJECT # | TOTAL INTENSITY |
| AREA | OPTICAL DENSITY |
| STANDARD AREA | RADIAL DISPERSION |
| COUNT | TEXTURE DIFFERENCE MOMENT |
| PERIMETER | EFA HARMONIC 2, SEMI-MAJOR AXIS |
| FIBER LENGTH | EFA HARMONIC 2, SEMI-MINOR AXIS |
| FIBER BREADTH | EFA HARMONIC 2, SEMI-MAJOR AXIS |
| SHAPE FACTOR | ANGLE |
| ELL. FORM FACTOR | EFA HARMONIC 2, ELLIPSE AREA |
| INNER RADIUS | EFA HARMONIC 2, AXIAL RATIO |
| OUTER RADIUS | EFA HARMONIC 3, SEMI-MINOR AXIS |
| MEAN RADIUS | |

The following results were obtained:
1,250 objects were counted
201 of those objects has standard area counts>2 (area>19000 pixels)
195 objects had areas<6000 pixels
1529 objects estimated in total
1328 object areas are>6000 pixels
The data was reduced to 917 objects that were 6000<area<19000
For the 917 objects a scatter plot of area vs. average intensity and a histogram of the average intensity were generated.
116 objects that had average intensity intensities>60 were manually looked at to determine their morphology.
Of those 116 objects:
  6 were dead or indistinguishable
  4 were interphase
  30 were prophase
  32 were metaphase
  24 were anaphase
  20 were telophase (10 pairs)
12 prophase objects were missed because of gray scale cut off. (8 of those prophase cells had gray scale values>57, as did 7 interphase)
1 telophase object was missed because it was too small (<6000)
1 prophase object was missed because it was too big (>1900)
16 mitotic objects were missed because they were parts of objects with standard count>2.

In sum, out of 917 single objects, the analysis correctly identified 106 out of 130 mitotic objects, or (81% predictive, 91% of identified mitotics). Out of 917 single objects, the analysis incorrectly identified only 10 non-mitotics as mitotics (1% total, 8% of identified mitotics); 14 mitotics as interphase (1.4% total, 1% interphase). Optionally, the next step is to develop an automated classification system which would automatically assign values to each object using these or other measurement features.

In a second experiment, the effects of Taxol on MDCK cells and the different types of morphological effects were observed. A plurality of MDCK cells grown in 96 well plates were treated with Taxol for 4.5 hours at different concentrations (10 μM–1pM). They were then fixed, labeled with Hoechst, and imaged.

This experiment used a labeling protocol comprising: MEOH fix at −20°, Wash in PBS, Block in PBS/BSA/Serum/Triton-X 100, Incubate with 5 μg/ml Hoechst 10 minutes, and wash.

Figure 9:
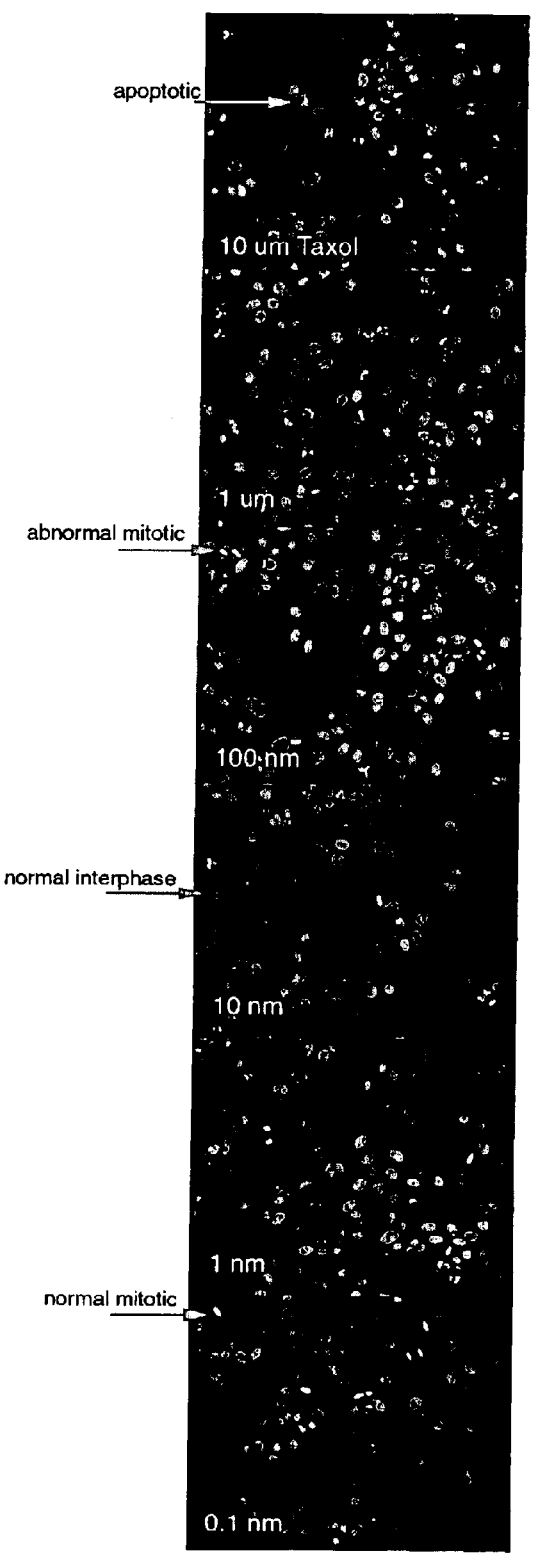
FIG. 9 illustrates example images for different types of morphologies in a particular experiment.
Figure 10:
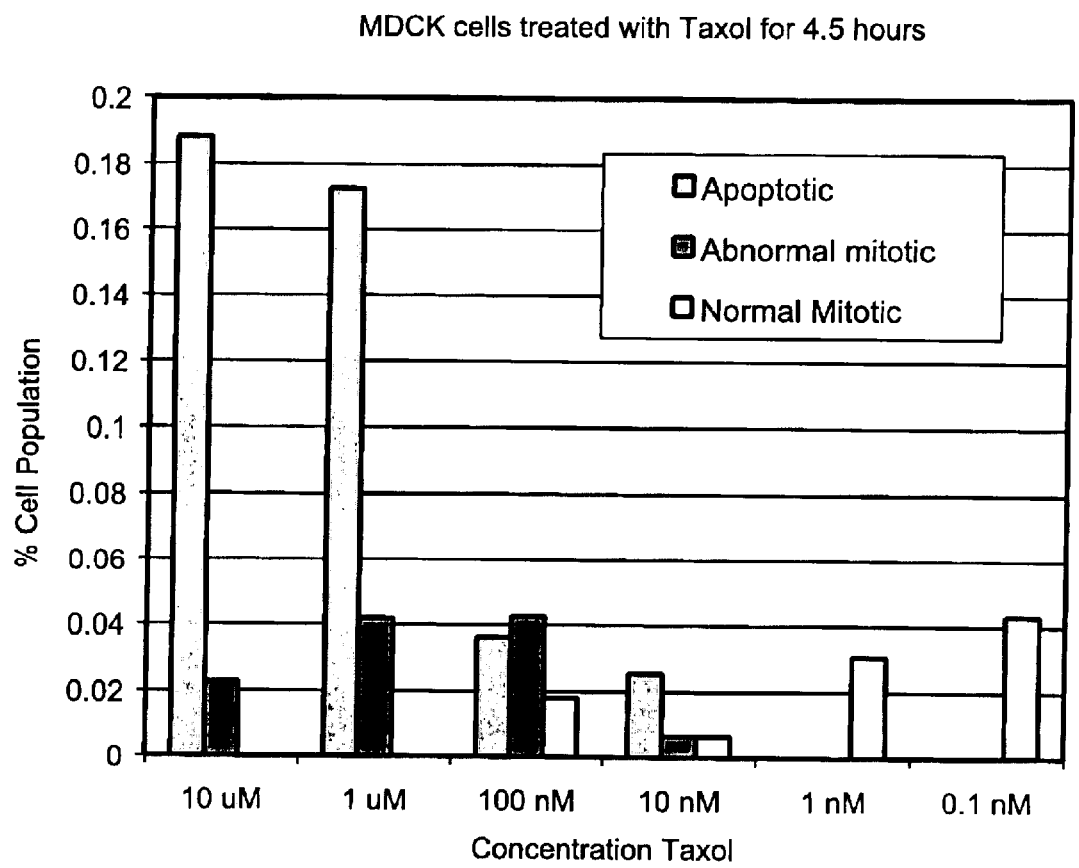
FIG. 10 illustrates a distribution of various morphologies in a cell population responsive to drug concentration in a particular experiment.

Cells were inspected for different morphologies and manually counted at each different drug concentration in one well. FIG. 9 shows example images from each drug concentration and the different types of morphologies and cells are highlighted. FIG. 10 shows the distribution of each morphology within the cell population as a function of drug concentration. The higher the concentration of Taxol, the larger proportion of cells underwent apoptosis, and the fewer number of normal mitotic cells were detected. The next step is to test the automated Hoechst analysis of the first experiment with multiple drugs.

In a third experiment, the purpose was to determine whether the automated analysis methods developed in the first experiment can detect differences in Hoechst morphology in the presence of 6 known compounds at one concentration and exposure time in one cell line. In this experiment, HeLa cells were separately treated with 6 compounds with known mechanism of action. The quantitative methods described in the first experiment were applied to the Hoechst images.

Approximately 5,000 HeLa cells per well were plated in a Costar black-walled 96 well tissue culture treated plate and left to recover in the incubator for 24 hours. After this time, 10 ug/mL of cytochalasin D (CD), Taxol, hydroxyurea, vinblastine, nocodazole, and staurosporine was added to different wells at a 1:100 addition in DMSO. The cells were incubated in the presence of drug for 24 more hours. After 24 hours, the cells were removed and fixed as in the first experiment. Then, 9 images per well were collected of the Hoechst staining using a 10× objective.

Figure 11:
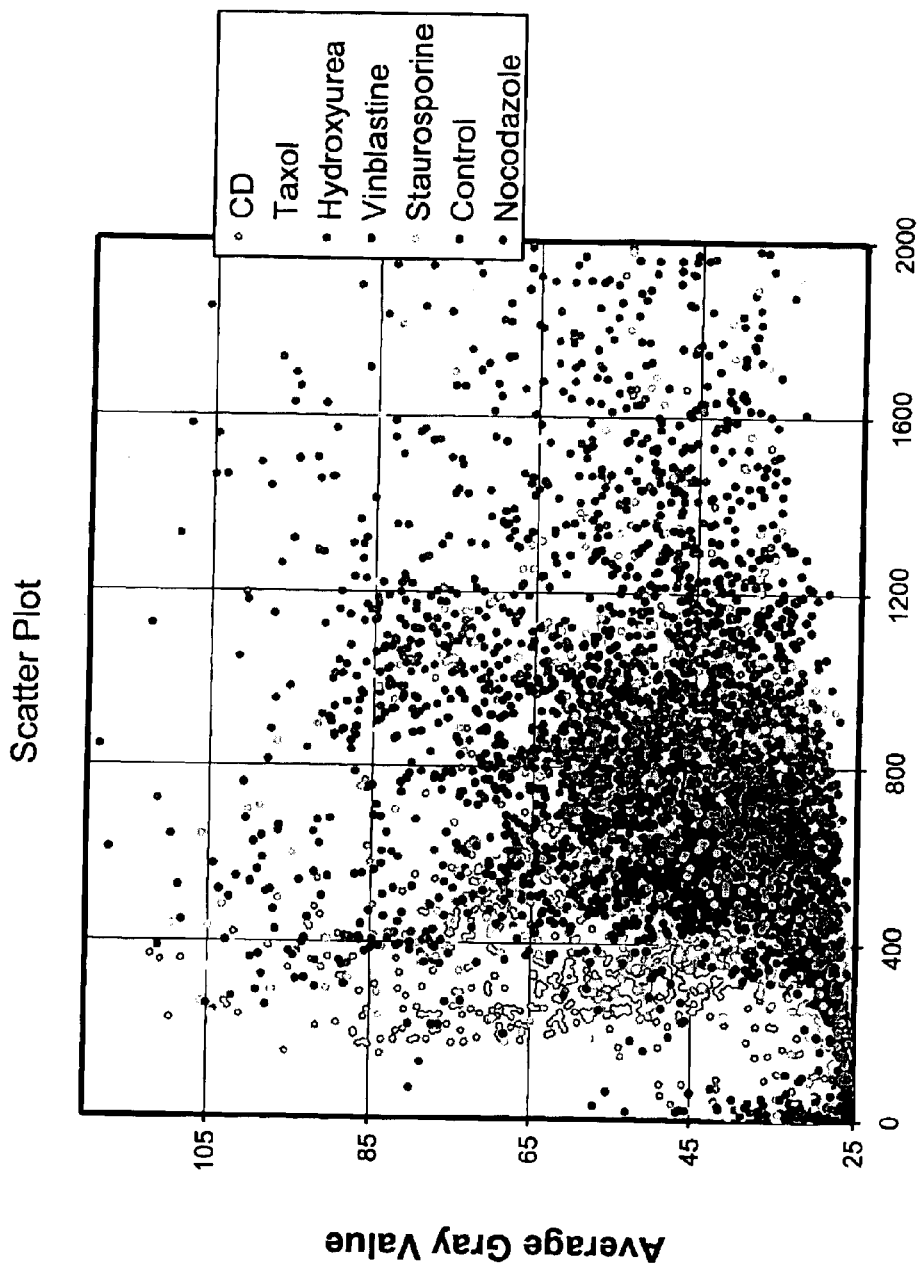
FIG. 11 illustrates a graph of quantified features of effects of manipulations on cells in a particular experiment.

The low magnification images taken of Hoechst were run through the automated image analysis method described in the first experiment. Plots of the average intensity and area were made of each compound. FIG. 11 shows the scatter plots of the compounds. The scatter plots of each compound are visually distinct. For example, cells treated with CD are smaller than control, and cells treated with Hydroxyurea are larger and brighter. Furthermore, the number of cells per well was very different (data not shown).

Based upon the results of this experiment, we conclude that our initial attempts at automatically identifying changes in cellular morphology show that we can clearly distinguish effects of different compounds. This method can also be used to count adherent cells.

The next experiment was to develop clustering algorithms that assign statistically meaningful values to the representative two dimensional data shown in FIG. 10, and even more complicated clustering of all of the multidimensional data that can be extracted across one, and multiple images.

A fourth experiment was performed to obtain high magnification images of two markers in the presence of drugs. In this experiment, HeLa cells were treated with 80 generic compounds with known mechanism of action. The quantitative methods described in the first experiment were applied to the Hoechst images.

Approximately 5,000 HeLa cells per well were plated in a Costar black walled 96 well tissue culture-treated plate and left to recover in the incubator for 24 hours. After this time, 10 ug/mL of each compound from the Killer Plate from Microsource Discovery Systems (Gaylordsville, Conn.) was added to different wells at a 1:100 addition in DMSO. The cells were incubated in the presence of drug for 24 more hours. After 24 hours, the cells were removed and fixed as in the first experiment. In addition to being labeled with Hoechst 33342 (against chromatin), cells were also labeled with 1 unit of rhodamine-conjugated phalloidin (against actin) for 30 minutes.

The 96 well plate was imaged twice. Once, 9 images per well were collected of the Hoechst staining using a 10× objective. After this, one image per well of both the phalloidin and Hoechst staining was collected using a 40× objective.

Figure 12:
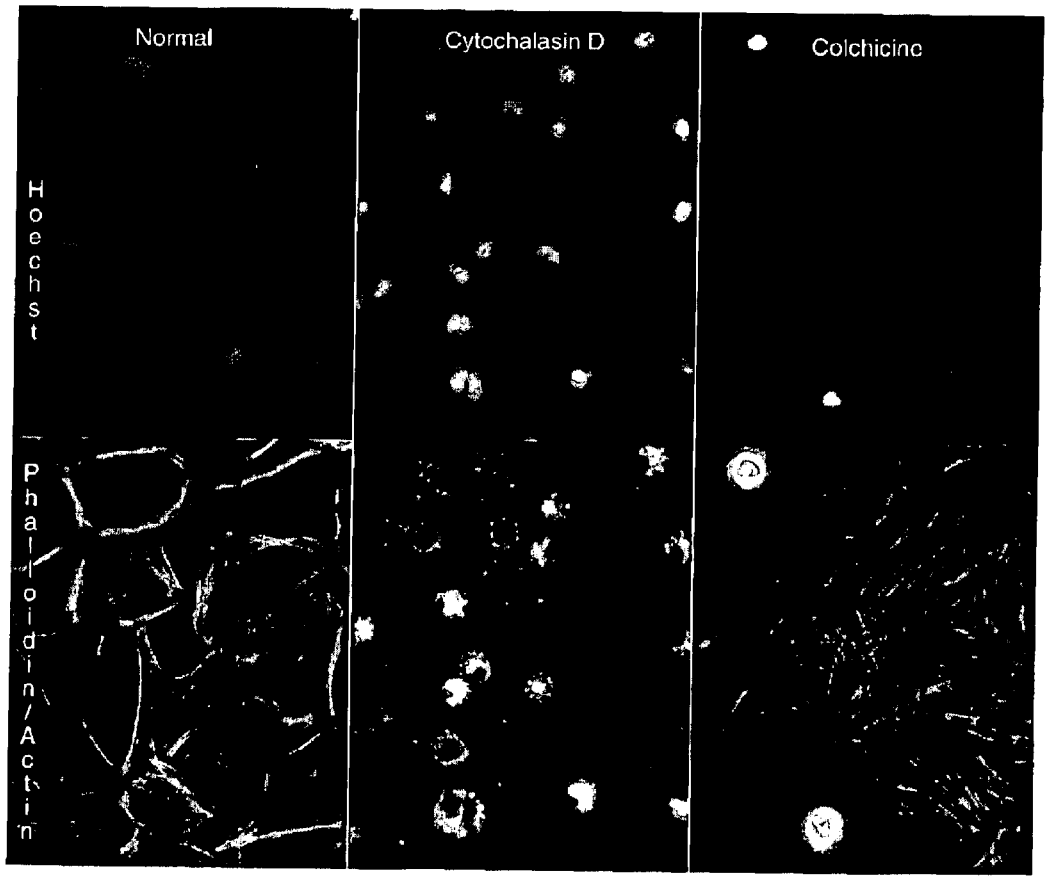
FIG. 12 illustrates effects of external agents on cells in a particular experiment.

The resulting high magnification images were analyzed qualitatively and distinct pattern differences were detected in both the Hoechst and phalloidin images. FIG. 12 shows three example images from the experiment. The top row is the Hoechst staining, and the bottom row is the phalloidin staining from the same well. The columns show the images from wells treated with just DMSO (control), cytochalasin D, and Colchicine. Notice that the morphology of each marker is different in the presence of each drug. Interestingly, there is an effect in the morphology of the chromatin in the Hoechst image of cytochalasin D, which directly targets the actin cytoskeleton (and thus there is an expected effect in the phalloidin image). Also, there is an effect on the actin cytoskeleton, compared to control, in the presence of colchicine that directly targets the microtubule network.

The low magnification images were analyzed as described in the first experiment, and different patterns were seen in both the average intensity vs. area plots, and in the number of cells per well (data not shown). Based upon the results of this experiment, we conclude that the fact that changes in patterns of a marker that is "down-stream" from the direct target of a compound are detectable illustrates the efficacy of this approach.

The next step based upon the results of this experiment is to develop automated image analysis protocols for actin and other markers.

A fifth experiment was performed to test quadruple labeling of 9 different cell lines grown in normal conditions. In this experiment, NCI-H460, A549, MDA-MD-231, MCF-7, SK-OV-3, OVCAR-3, A498, U-2 OS, and HeLa cells were plated. Then, the cells were fixed and stained for portions of the each cell known as DNA, tubulin, actin, and Golgi.

Cells were plated out at different densities for 48 hours. Cells were fixed and labeled by the above method. Cells were imaged using an automated imaging system that collected 9 images from each marker using a 10× objective. Higher magnification images were collected of a few cells for demonstration purposes.

Figure 13:
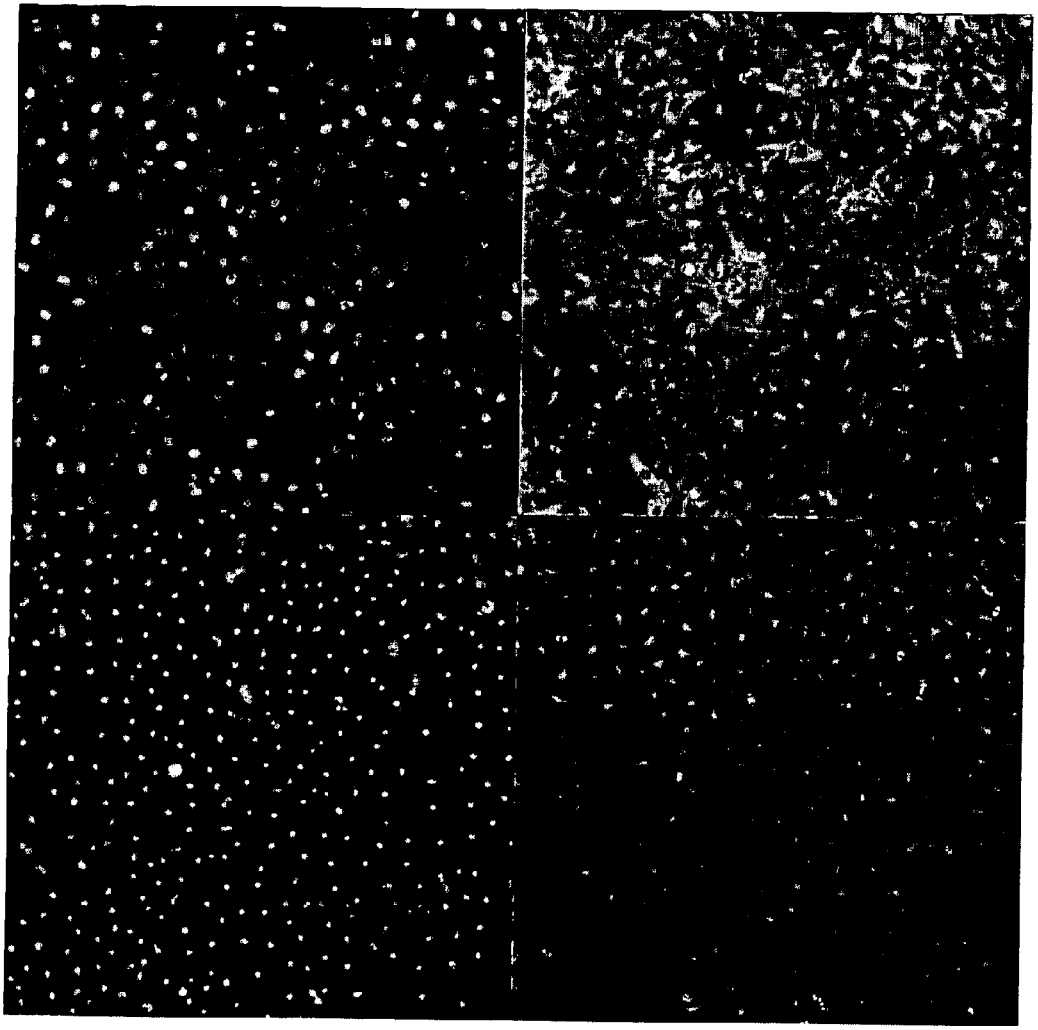
FIG. 13 illustrates 4 panels for each marker for a plurality of A549 cells in a particular experiment.
Figure 14:
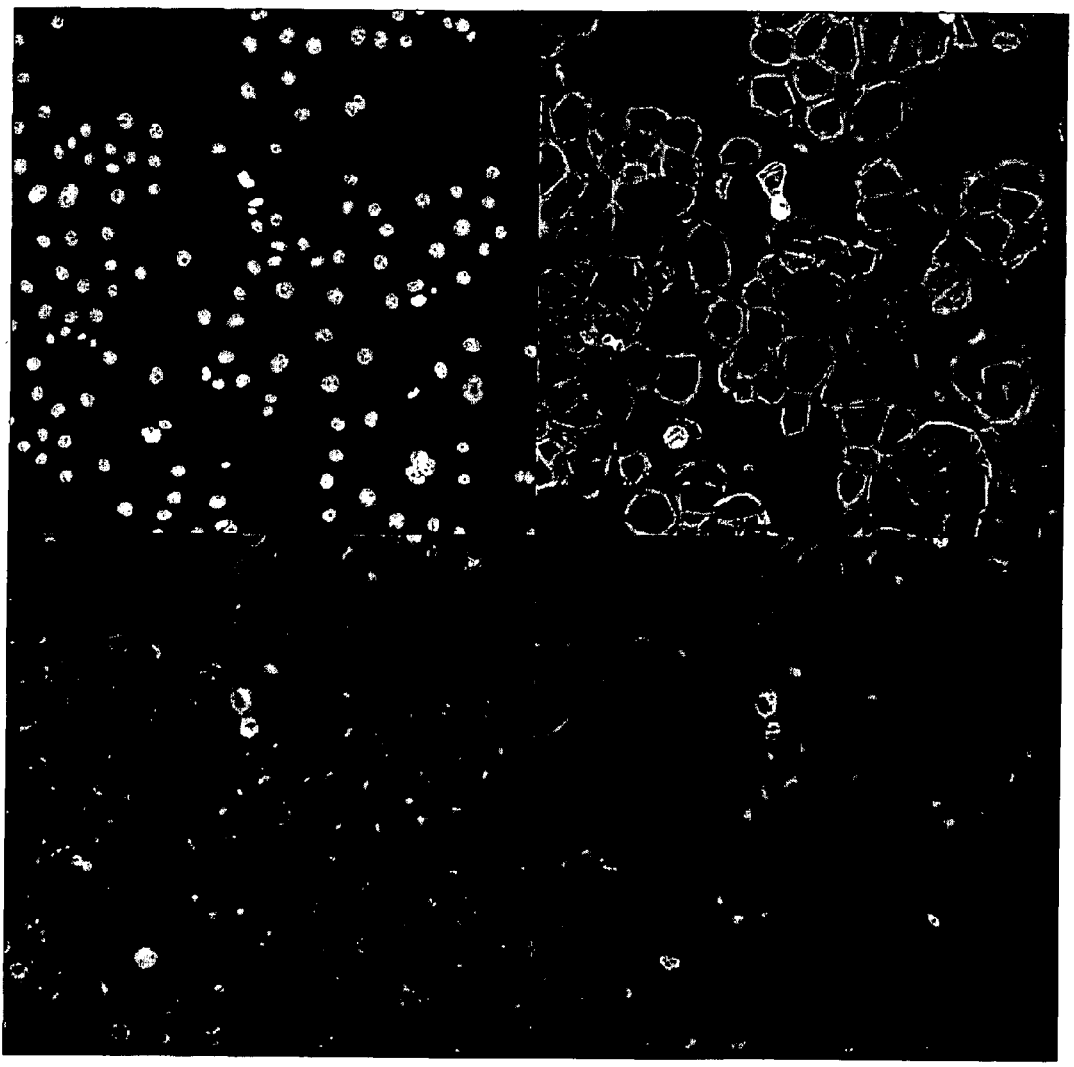
FIG. 14 illustrates 4 panels for each marker for a plurality of OVCAR-3 cells in a particular experiment.

In this experiment, each cell line demonstrated different morphological patterns as determined by phase. For example, A549 cells are much more compacted than OVCAR-3 cells as determined by phase contract imaging (data not shown). The different fluorescent markers showed even bigger differences between different cell lines. FIGS. 13 and 14 show 4 panels of each marker for A549 (FIG. 13) and OVCAR-3 cells (FIG. 14). The markers are Hoechst (upper left), Phalloidin (upper right), Lens culinaris (lower left), and DM1 a antibody (lower right). The following table summarizes the qualitative differences between these images:

| MARKER | A549 | OVCAR3 |
| --- | --- | --- |
| Hoechst/DNA | small | large |
| Phalloidin/actin | fuzzy | crisp - many stress fibers |
| Lens culinaris/Golgi | compact | Disperse/punctate |
| DM1alpha/Tubulin | perinuclear | evenly distributed |

Figure 15:
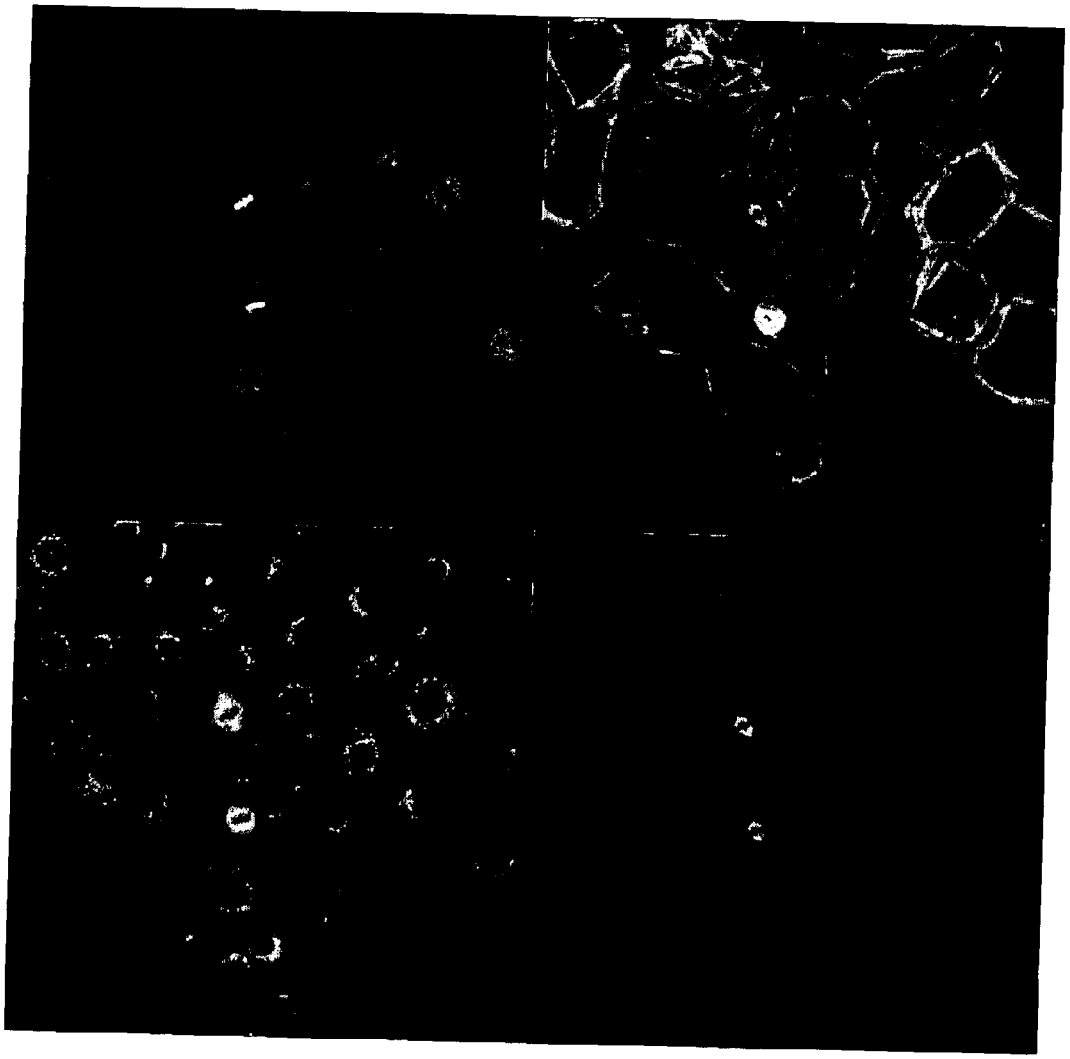
FIG. 15 illustrates 4 panels for each marker for a plurality of OVCAR-3 cells at 20× in a particular experiment.
Figure 16:
FIG. 16 illustrates 4 panels for each marker for a plurality of OVCAR-3 cells at 40× in a particular experiment.

Higher magnification images were taken of the OVCAR3 cells. FIG. 15 shows the same markers at 20×, and FIG. 16 shows the markers at 40×. While the highest magnification images show the most detail, these images illustrate that very little morphological or feature information is lost in the 10× images.

These data exemplify the differences in morphology seen between different cell types. Thus the automated image analysis software will have to be customized for each marker in each cell type. Different drugs should effect these morphologies differentially.

The next steps based upon the results of this experiment are to customize and develop an automated quantification for each marker and cell line.

A sixth experiment was conducted with a more sophisticated software package and to develop more flexible image recognition algorithms. In this experiment, prototype image features extraction was performed using MatLab programming language with image toolbox and SDC morphology toolboxes. Algorithms are being developed that will automatically identify objects on images and to measure various morphological and feature parameters of these objects. Since at present it is not known which of the measurements will be most useful for subsequent clustering, many different features for each of the cellular markers were acquired.

An example of a MatLab program called "AnalyseDNA" that takes as an input an unlimited number of images, identifies individual objects in these images based on either their intensities, or based on edge-detection algorithms, and extracts a number of morphological and intensity characteristics of these objects. A copy of this program is described in U.S. application Ser. No. 09/310,879, which has been noted.

Given the list of image files or montages of images as an input, this program creates an individual file for each image that contains the following quantitative measurements for all objects identified in the image:

```
 1 Index ("number" of an object);
 2 X coordinate of the center of
   mass;
 3 Y coordinate    "-"    ;
 4 Total Area (in pixels);
 5 Ratio of MajorAxis/MinorAxis;
 6 Eccentrisity;
 7 EquivDiameter;
 8 Solidity;
 9 Extent;
10 Total Intensity;
11 Avg. Intensity;
12 Median Intensity;
13 Intensity of 20% bright pixel
14 Intensity of 80% bright pixel
```

Figure 17:
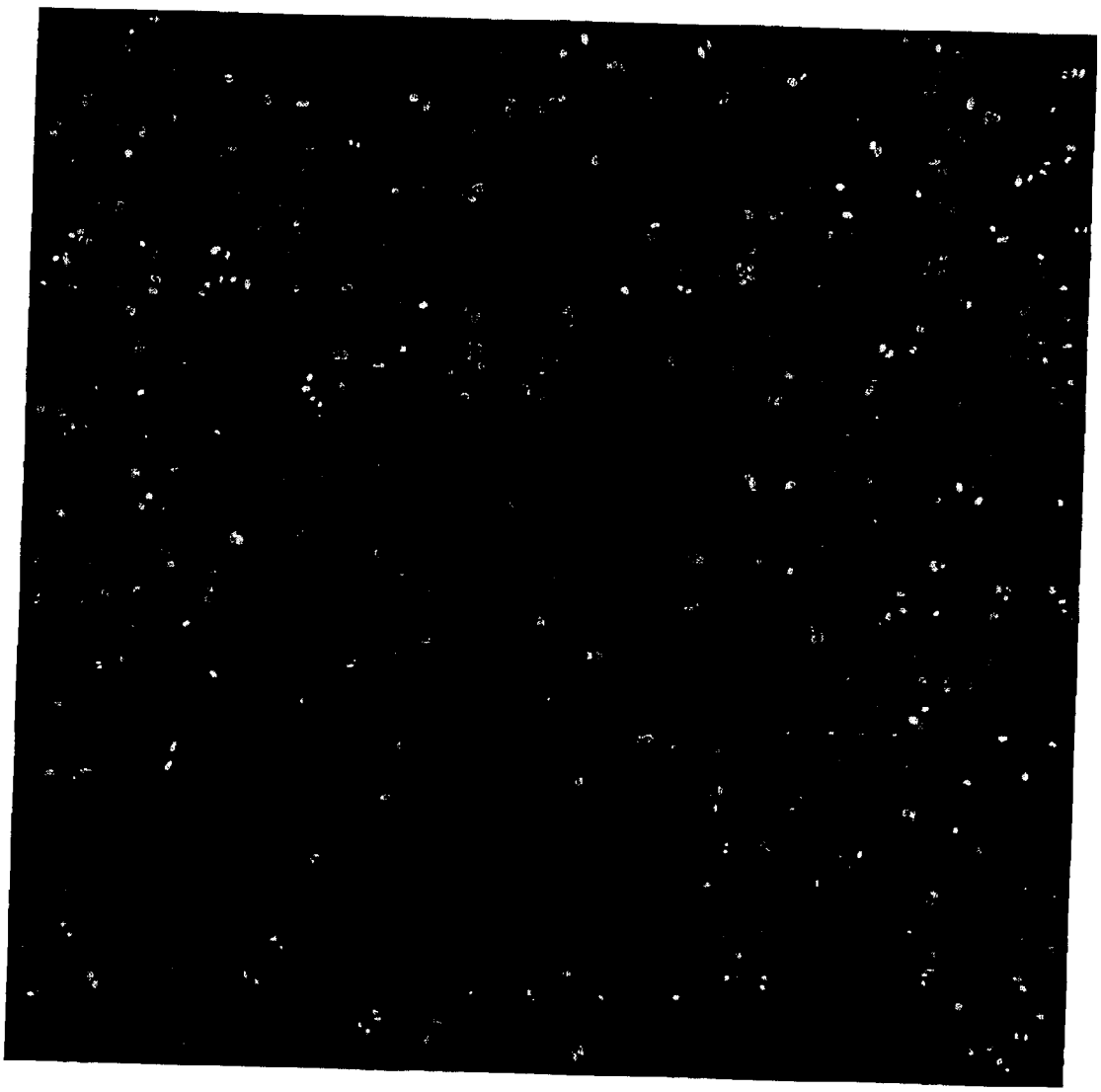
FIG. 17 illustrates a digital representation for a population module in a particular embodiment according to the present invention.

A fragment of an output for a single file, containing 9 images of cells stained for DNA and acquired with a 10× objective. A montage image that was used as a source to generate data presented on FIG. 17. The same program also summarizes measurements across many files and performs statistical analysis of the summary data. It creates a summary file with the following data:

```
 1 Image file number;
 2 Average object Area (in pixels);
 3 STD (standard deviation) of 2;
 4 Avg. of Ratio of MajorAxis/MinorAxis;
 5 STD of 4;
 6 Avg. Eccentrisity;
 7 STD of 6;
 8 Avg. EquivDiameter;
 9 STD of 8;
10 Avg. of Solidity;
11 STD of 10;
12 Avg. of Extent;
13 STD of 11
14 Avg. of objects Total Intensity;
15 STD of 14
16 Avg. of objects Avg Intensity;
16 STD of 15
18 Avg. of objects Median intensity;
19 STD of 18
20 Avg. of objects intensity of 20% bright pixel;
21 STD of 19
22 Avg. of objects intensity of 80% bright pixel;
23 STD of 21
```

An example of summary output obtained by running AnalyseDNA against 10 montage files also is shown in the aforementioned patent application.

A seventh experiment was conducted in order to use sequence analysis algorithms to analyze features of cell images. In this experiment, HeLa cells were treated for 24 hours with several different compounds, and then fixed, and stained with a fluorescent DNA dye. One image of these cells was acquired for each of the treatments and morphometric parameters and features were measured:

Resulting measurements were arranged into a string of numbers and reduced to a pseudo- nucleic acid sequence using following rules: At any given position in the sequence a number was substituted by "t" (a code for thymidine) if its value is among highest 25% of the values at the corresponding position in the data set, "g" if it is between 50% and 25%, "c" if it is between 75% and 50%, and "a" if it belongs to lowest 25% of values. Thus one descriptor or sequence was generated per treatment as illustrated in FIG. 18.

Resulting sequences were clustered using an AlignX module commercial software package Vector NTI, which uses a Neighbor Joining algorithm for sequence clustering.

Figure 19:
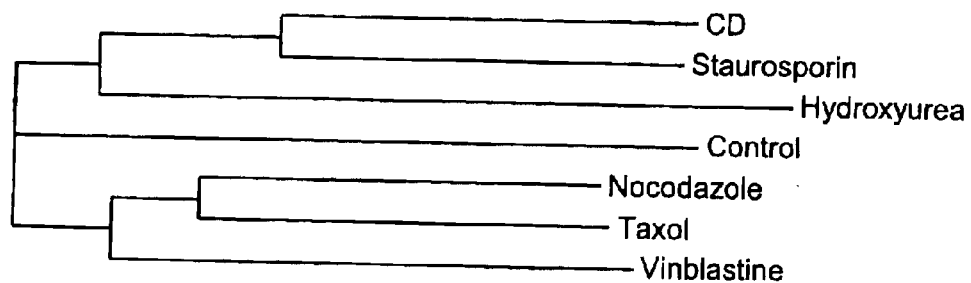
FIG. 19 shows another example of the generation of pseudo-sequences and clustering in a particular embodiment according to the present invention.

The resulting dendrogram is presented in FIG. 18. On the dendrogram, the closest "leafs" correspond to the closest pseudo-sequences. Interestingly, compounds with similar mechanisms of action cluster together on the dendrogram. Another example of the generation of pseudo-sequences and clustering is shown in FIG. 19.

In some embodiments, techniques according to the present invention can provide tools for the later stages of drug development such as clinical trial design and patient management. The properties of known drugs such as clinical trial and patient response information will be used in a similar fashion as the pre-clinical information to provide predictions about the properties of novel compounds. Because the human cell is the locus of drug action, a database containing drug-cell interactions can be able to provide predictive information for this aspect of drug development.

Although the above has generally described the present invention according to specific systems, the present invention has a much broader range of applicability. In particular, the present invention is not limited to a particular kind of data about a cell, but can be applied to virtually any cellular data where an understanding about the workings of the cell is desired. Thus, in some embodiments, the techniques of the present invention could provide information about many different types or groups of cells, substances, and genetic processes of all kinds. Of course, one of ordinary skill in the art would recognize other variations, modifications, and alternatives.

What is claimed is:

1. A system for capturing cellular information from a population of cells, the system comprising:
    an image acquisition system comprising a charged coupled camera adapted to capture an image of a plurality of manipulated cells, wherein the image acquisition system comprises a magnification of at least 1X or greater;
    an illumination apparatus comprising a flexible liquid light guide coupled to the image acquisition system for highlighting the plurality of manipulated cells, wherein the flexible liquid light guide is a flexible hose-type sleeve wherein said sleeve is filled with a liquid and wherein said liquid light guide is capable of vibrationally isolating the illumination apparatus from the image acquisition system wherein th illumination apparatus provides for an aquisition of the image of the plurality of manipulated cells and wherein said liquid light guide has less than about 30% transmission loss of the light at a remote location; and
    a database system coupled to the image acquisition system, the database system being adapted to be populated with information of the image of the plurality of manipulated cells;
    wherein the information comprises a plurality of descriptors, each of the descriptors comprising a plurality of features, each of the features corresponding to a cellular or subcellular component from the plurality of manipulated cells.

2. The system of claim 1 wherein the image is a digitized representation of the plurality of manipulated cells, the digitized representation highlighting each of the features of the plurality of manipulated cells.

3. The system of claim 1 wherein each of the features provides a characteristic selected from at least a count, area, perimeter, length, breadth, fiber length, fiber breadth, shape factor, elliptical form factor, inner radius, outer radius, mean radius, equivalent radius, equivalent sphere volume, equivalent prolate, volume, equivalent oblate volume, equivalent sphere surface, average intensity, total intensity, optical density, radial dispersion, texture difference, a population statistic value, and a spatial value of the plurality of manipulated cells.

4. The system of claim 1, wherein the liquid is an aqueous solution containing chloride or phosphate.

5. The system of claim 1, wherein the liquid light guide further comprises a thin layer on the inside of the sleeve.

6. The system of claim 5, wherein said layer comprises tetrafluoroethylene and mexafluoropropylene.

7. The system of claim 5, wherein said layer comprises tetrafluoroethylene and perfluoromethyl vinyl ether.

8. The system of claim 5, wherein said layer comprises tetrafluoroethylene and perfluoropropyl vinyl ether.

9. The system of claim 1 further comprising a stage comprising a device for moving the cell holder in a spatial direction.

10. The system of claim 1 further comprising a computing device connected between the database system and the image acquisition system.

11. The system of claim 1 wherein the database system is selected from an objected oriented database, a relational database and a mixed database.

12. The system of claim 1, further comprising a filter wheel having a plurality of filters.

13. The system of claim 1, further comprising software that controls operation of the image acquisition system.

14. The system of claim 1, further comprising software for acquiring multi-wavelength images from multiple sites on one multi-well plate, sequentially naming image files, and logging any imaging parameter information with image files.

* * * * *